United States Patent
Kato et al.

(10) Patent No.: US 6,238,752 B1
(45) Date of Patent: May 29, 2001

(54) DIAMINO COMPOUNDS, POLYAMIC ACIDS, POLYIMIDES, LIQUID CRYSTAL ALIGNING FILMS USING SAID POLYIMIDE FILMS AND LIQUID CRYSTAL DISPLAY DEVICES USING SAID ALIGNING FILMS

(75) Inventors: Takashi Kato, Chiba-Ken; Nobuyuki Otsuka, Kanagawa-Ken; Shizuo Murata, Chiba-Ken; Hideo Sato, Kanagawa-Ken, all of (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/403,597
(22) PCT Filed: Jul. 23, 1999
(86) PCT No.: PCT/JP99/03948
§ 371 Date: Oct. 22, 1999
§ 102(e) Date: Oct. 22, 1999
(87) PCT Pub. No.: WO00/06543
PCT Pub. Date: Feb. 10, 2000

(30) Foreign Application Priority Data

Jul. 29, 1998 (JP) .................................................. 10-228710

(51) Int. Cl.[7] .................................................. G02F 1/1337
(52) U.S. Cl. ........................ 428/1.26; 428/1.23; 428/1.27; 428/473.5; 548/548; 548/547; 528/353
(58) Field of Search .................................. 428/1.26, 1.27, 428/1.23, 473.5; 528/353, 125, 350, 128, 170, 172, 173, 176, 183, 188, 220, 229; 548/548, 547

(56) References Cited

FOREIGN PATENT DOCUMENTS

| | | |
|---|---|---|
| 51-13198 | 4/1976 | (JP) . |
| 63-1379 23 | * 6/1988 | (JP) . |
| 2608661 | 2/1997 | (JP) . |
| WO00/06543 | 10/2000 | (WO) . |

OTHER PUBLICATIONS

Jpn. J. Appl. Phys. vol. 31 (1992) pp. 2155–2164—Part 1 No. 7, Jul. 1992.

* cited by examiner

Primary Examiner—Alexander S. Thomas
(74) Attorney, Agent, or Firm—McDermott, Will & Emery

(57) ABSTRACT

This invention relates to a diamino compound represented by the formula [1]:

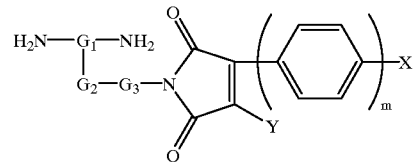

in which $G_1$ is a trivalent organic group of 2–20 carbon atoms, $G_2$ is independently a single bond, —COO—, —OCO—, —NHCO—, —CONH—, —O—, —O—, or —CO—, $G_3$ is a single bond or an alkylene group of 1–20 carbon atoms, X and Y are each independently a hydrogen atom, a fluorine atom, a chlorine atom, a cyano group, a nitro group, or an alkyl group, a haloalkyl group, an alkoxy group or a haloalkoxy group, each alkyl or alkoxy group having 1–12 carbon atoms, or a cycloalkyl group of 3–8 carbon atoms or a trans-4-alkylcyclohexyl group of 9–14 carbon atoms, and m is an integer of 0–3; a polyamic acid and polyimide using the said diamino compound, an aligning film using the said polyimide and a liquid crystal display device using the said aligning film. The aligning film is prepared by irradiation of a polarized ultraviolet light to the polyimide film.

15 Claims, No Drawings

DIAMINO COMPOUNDS, POLYAMIC ACIDS, POLYIMIDES, LIQUID CRYSTAL ALIGNING FILMS USING SAID POLYIMIDE FILMS AND LIQUID CRYSTAL DISPLAY DEVICES USING SAID ALIGNING FILMS

TECHNICAL FIELD

This invention relates to a diamino compound having a photosensitive group in the side chain thereof, a polyamic acid and a photo crosslinking polyimide, a liquid crystal aligning film using said polyimide, and a liquid crystal display device using said aligning film.

BACKGROUND ART

Recently, there have been demands for the display of word processors, notebook computers, etc. to have a lighter weight and a thinner thickness and to consume less electric power, and a superior liquid crystal display device is expected to be developed for a flat display satisfying these requirements. A liquid crystal display device is provided with a liquid crystal aligning film having a predetermined pretilt angle so as to align liquid crystal molecules to a given direction. As a method for preparing such aligning films, a rubbing process wherein a thin film of a polymeric compound such as a polyimide formed on a substrate is rubbed toward a certain direction with a cloth such as rayon, a process wherein silicon dioxide is subjected to oblique evaporation, etc. are known.

However, although the rubbing process has been widely applied in the industrial field as a convenient and inexpensive process, it has the problems of the formation of dusts, the generation of static electricity and the like.

The oblique evaporation process costs too much to be scaled up.

Under these circumstances, a photo-orientation process has recently attracted attention of the industry. In such a process for the preparation of an aligning film according to this photo-orientation method, a thin film of a photosensitive polymeric compound is formed on a substrate and a polarized ultraviolet light or a laser light is irradiated thereto, whereby only the photosensitive groups in line with the irradiated polarized light may photochemically react to develop anisotropy on the aligning film and align liquid crystal molecules. This process can provide the advantages of no generation of static electricity or no contamination of impurities because the other members are not in contact with the thin film coated over the substrate.

Several photo-aligning films utilizing photodimerization of a polarized light irradiated to polyvinyl cinnamate and derivatives thereof are disclosed, for example, in M. Schadt et al., Jpn. J. Appl. Phys., 31, 2155 (1992) or Japanese Patent No. 2608661. However, these aligning films have the drawbacks of a low heat stability, an inferior retention of shape and an easily turbulent alignment of liquid crystal.

Vinyl polymers having arylmaleimide residues in the side chain thereof are disclosed as a photosensitive group having a higher sensitivity in Japanese Patent Publication No. 13198/1976 and so on, but no examples of utilizing them as an aligning film for liquid crystal display device is disclosed therein.

The present inventors have made earnest studies, and as a result, have found out that a polyimide having an β,β-substituted maleimide group in the side chain thereof may be rapidly dimerized in the side chain thereof at a high sensitivity, and that the crosslinked film is excellent in a heat stability and a retention of shape and also shows a favorable alignment of liquid crystal, upon which this invention has been completed.

DISCLOSURE OF INVENTION

More specifically, the constitution of this invention is as described below.

(1) A diamino compound represented by the formula [1]:

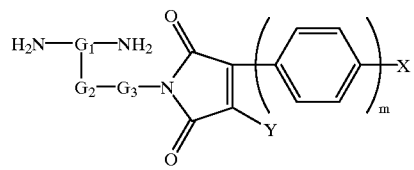

in which $G_1$ is a trivalent organic group of 2–20 carbon atoms, $G_2$ is independently a single bond, —COO—, —OCO—, —NHO—, —CONH—, —O—, —S—, or —CO—, $G_3$ is a single bond or an alkylene group of 1–20 carbon atoms, X and Y are each independently a hydrogen atom, a fluorine atom, a chlorine atom, a cyano group, a nitro group, or an alkyl group, a haloalkyl group, an alkoxy group or a haloalkoxy group, each alkyl or alkoxy group having 1–12 carbon atoms, or a cycloalkyl group of 3–8 carbon atoms or a trans-4-alkylcyclohexyl group of 9–14 carbon atoms, and m is an integer of 0–3.

(2) A polyamic acid which comprises a structural unit represented by the formula [2]:

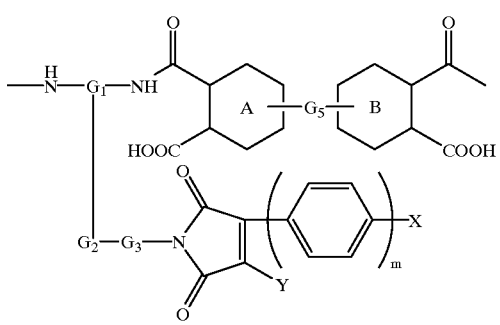

in which $G_1$, $G_2$, $G_3$, X and Y are as defined above, $G_5$ is independently a single bond, or a bond of —CH$_2$—, —O—, —CO—, —SO$_2$—, —C(CH$_3$)$_2$— or —C(CF$_3$)$_2$—, and rings A and B are each independently a benzene ring or a cyclohexane ring; and has a logarithmic viscosity number of 0.1–5.0 dl/g as measured in N-methyl-2-pyrrolidone at the concentration of 0.5 g/dl at the temperature of 30±0.01° C.

(3) A polyamic acid which comprises a structural unit represented by the above formula [2] and a structural unit represented by the formula [3]:

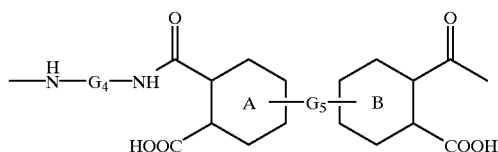

in which $G_6$ is independently a single bond, or a bond of —$CH_2$—, —O—, —CO—, —$SO_2$—, —$C(CH_3)_2$— or —$C(CF_3)_2$—, rings A and B are each independently a benzene ring or a cyclohexane ring, and $G_4$ is a divalent organic group of 2–36 carbon atoms or a polysiloxane group of the formula [4]:

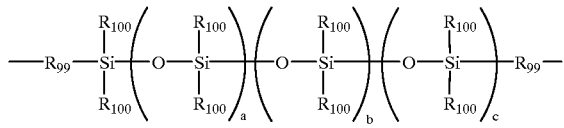

in which $R_{99}$ is an alkylene group of 1–6 carbon atoms or a phenylene group, $R_{100}$ independently may be the same or different and is an alkyl group of 1–3 carbon atoms or a phenyl group, and a, b, and c are 0 or a positive number with a relation of $1 \leq a+b+c \leq 100$; and has a logarithmic viscosity number of 0.1–5.0 dl/g as measured in N-methyl-2-pyrrolidone at the concentration of 0.5 g/dl at the temperature of 30±0.01° C.

(4) A polyimide obtained by imidation of the polyamic acid as disclosed in the above (2) or (3) and subsequent irradiation of a polarized ultraviolet light.

(5) An aligning film for a liquid crystal display device using a thin film comprising the polyimide as disclosed in the above (4).

(6) An aligning film for a liquid crystal display device which is obtained by imidation of the polyamic acid as disclosed in the above (2) or (3), subsequent irradiation of a polarized ultraviolet light and the resulting photoreaction of a portion of the polyimide side chains.

(7) A liquid crystal display device which comprises an aligning film for a liquid crystal display device as disclosed in the above (4)–(6).

(8) A liquid crystal display device as disclosed in the above (7) wherein a liquid crystal composition comprises at least one compound selected from the group consisting of the compounds of the formulae [5], [6] and [7]:

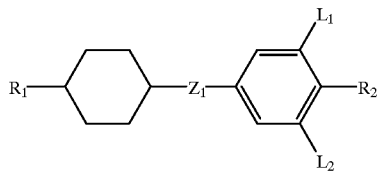

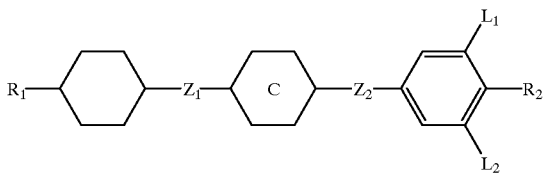

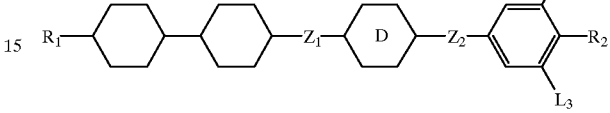

in which $R_1$ is an alkyl group of 1–10 carbon atoms wherein any non-adjacent methylene groups may be substituted with —O— or —CH=CH— and any hydrogen atoms may be substituted with fluorine atoms; $R_2$ is a fluorine atom, a chlorine atom, —$OCF_3$, —$OCF_2H$, —$CF_3$, —$CF_2H$, —$CFH_2$, —$OCF_2CF_2H$ or —$OCF_2CFHCF_3$; $L_1$ and $L_2$ are each independently a hydrogen atom or a fluorine atom; $Z_1$ and $Z_2$ are each independently 1,2-ethylene, 1,4-butylene, —COO—, —$CF_2O$—, —$OCF_2$—, —CH=CH— or a single bond; ring C is trans-1,4-cyclohexylene, 1,3-dioxane-2,5-diyl or 1,4-phenylene wherein a hydrogen atom may be substituted with a fluorine atom; and ring D is trans-1,4-cyclohexylene or 1,4-phenylene wherein a hydrogen atom may be substituted with a fluorine atom.

(9) A liquid crystal display device as disclosed in the above (7) wherein a liquid crystal composition comprises at least one compound selected from the group consisting of the compounds of the formulae [8] and [9]:

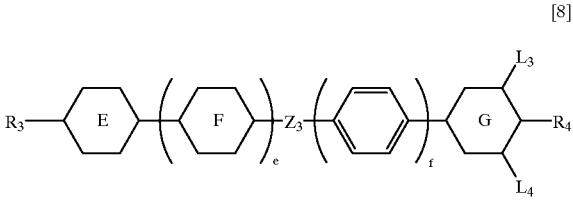

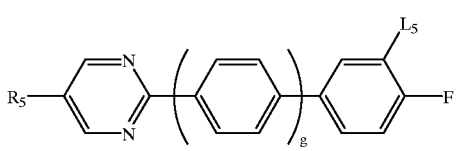

in which $R_3$ and $R_5$ are each independently an alkyl group of 1–10 carbon atoms wherein any non-adjacent methylene groups may be substituted with —O— or —CH=CH— and any hydrogen atoms may be substituted with fluorine atoms; $R_4$ is a group of —CN or —C≡C—CN; ring E is trans-1,4-cyclohexylene, 1,4-phenylene, 1,3-dioxane-2,5-diyl or pyrimidine-2,5-diyl; ring F is trans-1,4-cyclohexylene, 1,4-phenylene wherein a hydrogen atom may be substituted with a fluorine atom, or pyrimidine-2,5-diyl; ring G is trans-1,4-cyclohexylene or 1,4-phenylene; $Z_3$ is 1,2-ethylene, —COO—, or a single bond; $L_3$, $L_4$ and $L_5$ are each independently a hydrogen atom or a fluorine atom; and e, f and g are each independently 0 or 1.

(10) A liquid crystal display device as disclosed in the above (7) wherein a liquid crystal composition comprises at least one compound selected from the group consisting of the compounds of the formulae [10], [11] and [12]:

[10]

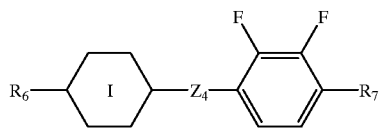

[11]

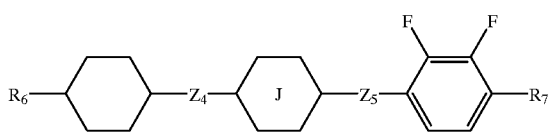

[12]

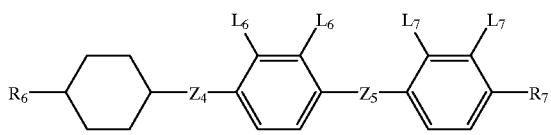

in which $R_6$ and $R_7$ are each independently an alkyl group of 1–10 carbon atoms wherein any non-adjacent methylene groups may be substituted with —O— or —CH=CH— and any hydrogen atoms may be substituted with fluorine atoms; rings I and J are each independently trans-1,4-cyclohexylene or 1,4-phenylene; $L_6$ and $L_7$ are each independently a hydrogen atom or a fluorine atom, provided that they do not simultaneously represent hydrogen atoms; and $Z_4$ and $Z_5$ are each independently 1,2-ethylene, —COO—, or a single bond.

(11) A liquid crystal display device as disclosed in the above (7) wherein a liquid crystal composition comprises at least one compound selected from the group consisting of the compounds of the said formulae [5], [6] and [7], and as a second component at least one compound selected from the group consisting of the compounds of the formulae [13], [14] and [15]:

[13]

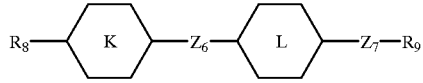

[14]

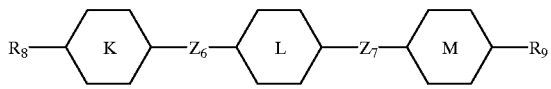

[15]

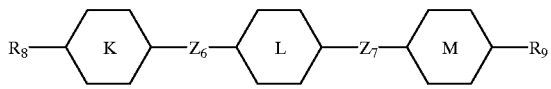

in which $R_8$ and $R_9$ are each independently an alkyl group of 1–10 carbon atoms wherein any non-adjacent methylene groups may be substituted with —O— or —CH=CH— and any hydrogen atoms may be substituted with fluorine atoms; rings K, L and M are each independently trans-1,4-cyclohexylene, pyrimidine-2,5-diyl or 1,4-phenylene wherein a hydrogen atom may be substituted with a fluorine atom; and $Z_6$ and $Z_7$ are each independently 1,2-ethylene, —C≡C—, —COO—, —CH=CH— or a single bond.

(12) A liquid crystal display device as disclosed in the above (7) wherein a liquid crystal composition comprises at least one compound selected from the group consisting of the compounds of the said formulae [8] and [9], and as a second component at least one compound selected from the group consisting of the compounds of the said formulae [13], [14] and [15].

(13) A liquid crystal display device as disclosed in the above (7) wherein a liquid crystal composition comprises at least one compound selected from the group consisting of the compounds of the said formulae [10], [11] and [12], and as a second component at least one compound selected from the group consisting of the compounds of the said formulae [13], [14] and [15].

(14) A liquid crystal display device as disclosed in the above (7) wherein a liquid crystal composition comprises at least one compound selected from the group consisting of the compounds of the said formulae [5], [6] and [7], as a second component at least one compound selected from the group consisting of the compounds of the said formulae [8] and [9] and as a third component at least one compound selected from the group consisting of the compounds of the said formulae [13], [14] and [15].

(15) A liquid crystal display device as disclosed in the above (8)–(14) wherein a liquid crystal composition further comprises one or more of optically active compounds.

The diamine of this invention may be represented by the above formula [1]. The structure of the moiety $G_1$ in the formula [1] is not particularly restricted as far as it is a trivalent organic group of 2–20 carbon atoms. Specific examples thereof are the following groups:

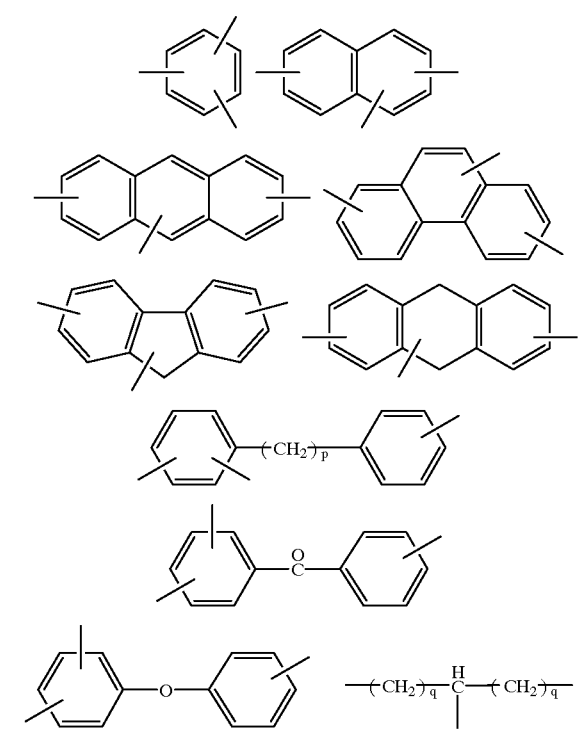

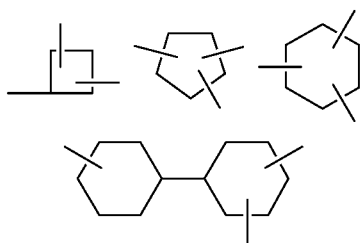

in which p is an integer of 0–10 and q is an integer of 1–10. Of these groups,

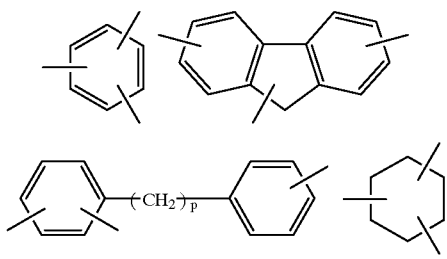

are preferable and most preferable is

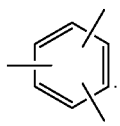

In the diamino compound of this invention represented by the formula [1], the group $G_1$ in the diamine moiety is bound to the photosensitive moiety via the linking group $G_2$. Accordingly, in the preparation of the compound, if both the diamine moiety and the photosensitive base moiety have functional groups capable of reacting each other, the reaction may be performed by utilizing said functional groups for linking both moieties. Unless either moiety has such groups, necessary functional groups may be first introduced into the moieties, which are allowed to react and link together. These linking reactions will be briefly illustrated below in line with the sort of $G_2$. The synthesis may be performed according to any well-known methods, such as a dehydration reaction of a carboxyl group and a hydroxyl group for an ester bond, a dehydration reaction of an amino group and a carboxyl group for an amide bond, a removal of a sodium salt with a sodium alcoholate and a halide for an ether bond, a conversion of both groups to an alkyl halide and subsequent dehalogenation with potassium sulfide for a sulfide bond, a reaction of a cyano group with Grignard reagent and subsequent hydrolysis for a carbonyl bond, and a dehydration reaction between an alcohol with an α-arylmaleimide for a single bond.

A specific example of a process for the preparation of a diamino compound is the process in the case where $G_2$ is a single bond, wherein a dinitroalcohol and an arymaleimide are subjected to a dehydration reaction such as Mitsunobu reaction to form a dinitroalkylene-α-arylmaleimide and the nitro group thereof is reduced with a metal such as tin or iron and conc. hydrochloric acid to produce a diamino compound. This may be illustrated by the following reaction scheme.

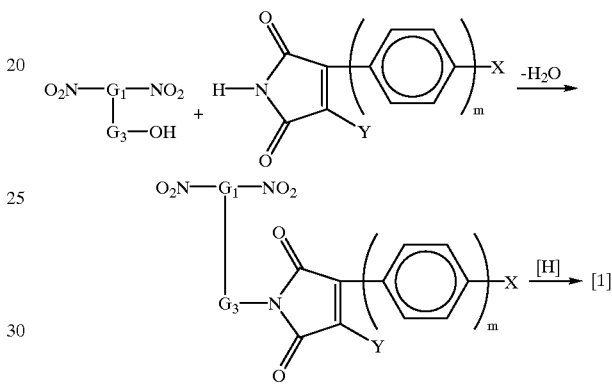

In the case where $G_2$ is an ester bond, an acid chloride is synthesized from a dinitrocarboxylic acid with thionyl chloride or phosphorus pentachloride, while a hydroxyalkyl-α-arylmaleimide is synthesized by the reaction of an arylmaleic anhydride with an amino alcohol. Both products are condensed in the presence of a base such as triethylamine or pyridine to form a dinitroester, and then the nitro group thereof may be similarly reduced as described above. The reaction scheme will be shown below.

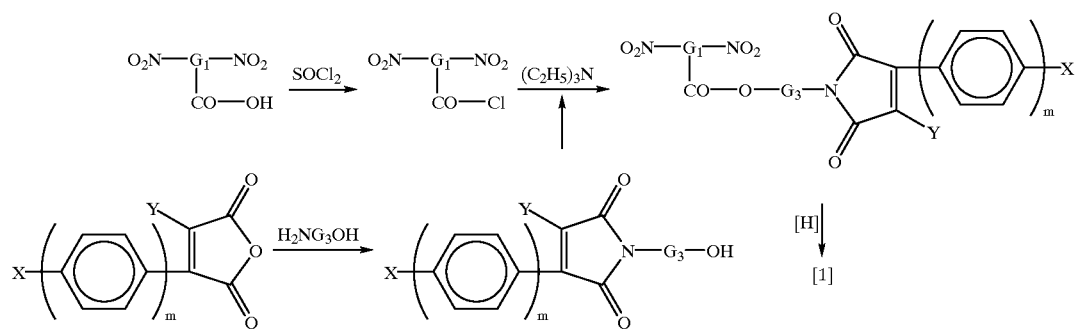

In the case where $G_3$ is an ether bond, a hydroxyalkyl-α-arylmaleimide is synthesized by the reaction of an arylmaleic anhydride with an amino alcohol. The hydroxyl group of this compound is halogenated by thionyl chloride, phosphorus trichloride, etc. to form a haloalkyl-α-arylmaleimide. This product is reacted with a dinitroalcohol or phenol in the presence of a base such as potassium carbonate and sodium hydride to form a dinitroether, which is then reduced to form the final compound. This is shown by the following reaction scheme.

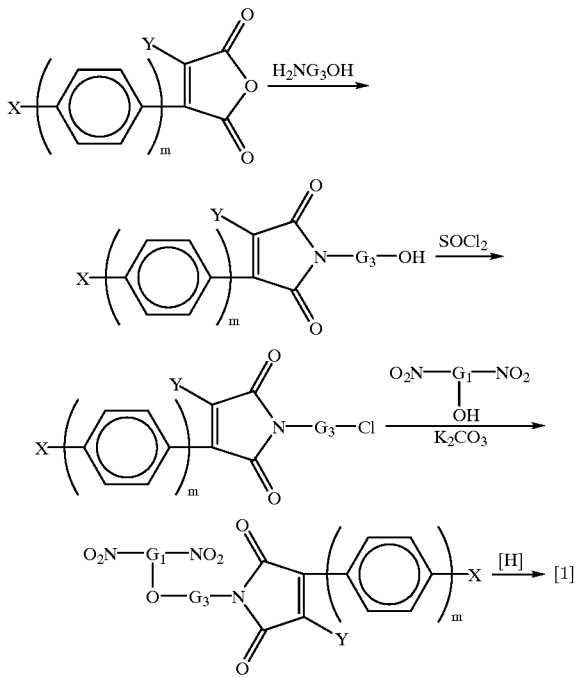

Of the above linking groups $G_2$, a single bond, an ester bond and an ether bond are more preferable and a single bond is particularly preferred.

The diamino compound synthesized as described above which has an α,β-substituted maleimide residue in the side chain thereof may be subjected to the polymerization reaction with a tetracarboxylic dianhydride represented by the formula [16]:

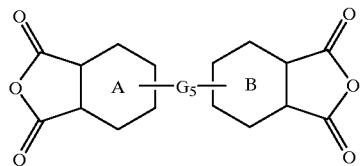

wherein $G_5$, ring A and ring B are as defined above; while retaining said maleimide group, to afford a solution of a polyamic acid having an α,β-substituted maleimide residue in the side chain thereof. This polyamic acid is subjected to imidation by any publicly known method such as heating or chemical dehydration and then irradiated with a polarized ultraviolet light to afford the polyimide of this invention. The maleimide residues may be polymerized by irradiation of said polarized ultraviolet light and the polymeric product may be used as an aligning film without any rubbing treatment. The aligning film for liquid crystal display device according to this invention is prepared by coating a solution of the present polyamic acid having an α,β-substituted maleimide residue in the side chain thereof over a substrate, imidating by heating or the like, and then irradiating a polarized ultraviolet light to provide the film surface with anisotropy.

As alternative embodiment of this invention, a polyamic acid comprising the structural units of [2] and [3] may be mentioned. Another diamine as illustrated hereafter is added to a diamino compound represented by the formula [1] to form diamine components, which may be reacted as described above with a tetracarboxylic dianhydride represented by the formula [17]:

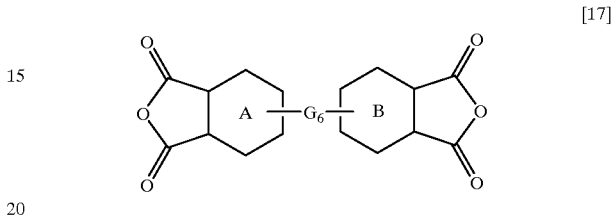

wherein $G_6$, ring A and ring B are as defined above; to obtain the polyamic acid, and further, the polyimide.

The diamines which may provide a divalent organic group of 2–36 carbon atoms as $G_4$ may include the following compounds, but are not particularly limited thereto.

More specifically, they may include aliphatic diamines such as trimethylenediamine, tetramethylenediamine, hexamethylenediamine, 4,4-dimethylheptamethylenediamine and 2,11-dodecanediamine; aromatic diamines such as bis(4-aminophenyl) ether, bis (4-aminophenyl)methane, bis (4-amino-3-methylphenyl)methane, bis(4-amino-3,5-dimethylphenyl)methane, bis(4-aminophenyl)sulfone, bis (4-aminophenyl)sulfide, bis(4-(3-aminophenoxy)phenyl) sulfone, 2,2-bis(4-(4-aminophenoxy)phenyl)propane, bis(4-(4-aminophenoxy)phenyl)sulfone, 1,2-diaminobenzene, 1,3-diaminobenzene, 1,4-diaminobenzene, 1,4-diamino-2-butylbenzene, 1,4-diamino-2-dodecyloxybenzene, benzidine, 2,2-diaminobenzophenone, 4,4-diaminobenzophenone, 2,2-bis(4-aminophenyl)propane, 1,5-diaminonaphthalene, 4,4-diamino-3-octyldiphenylmethane, 2,2-bis(4-(4-aminophenoxy) phenyl)-1,1,1,3,3,3-hexafluoropropane, 4,4-bis(4-aminophenoxy)biphenyl, 1,2-bis(4-aminophenyl)ethane, 1,2-bis( 4-amino-2-methylphenyl)ethane, 1,1-bis(4-(4-aminophenoxy)phenyl)cyclohexane, 1,1-bis(4-(4-aminophenoxy)phenyl)-4-propylcyclohexane, 1,1-bis(4-(4-aminobenzyl)phenyl)cyclohexane, 1,3-bis(4-(4-aminobenzyl)phenyl)propane and 1,4-bis(4-aminophenoxy) benzene, bis-p-aminophenylaniline; alicyclic diamines such as 1,4-diaminocyclohexane, 4,4-diaminodicyclohexylmethane, 4,4-diamino-3,3-dimethyldicyclohexylmethane and 4,4-diamino-3,3-dimethyldicyclohexyl, etc. These compounds may include isomers thereof and a mixture of these isomers may be similarly used. A combination of two or more of these compounds may also be used.

As specific examples of diamines which have a polysiloxane as the skelton thereof, the following compounds may be illustrated:

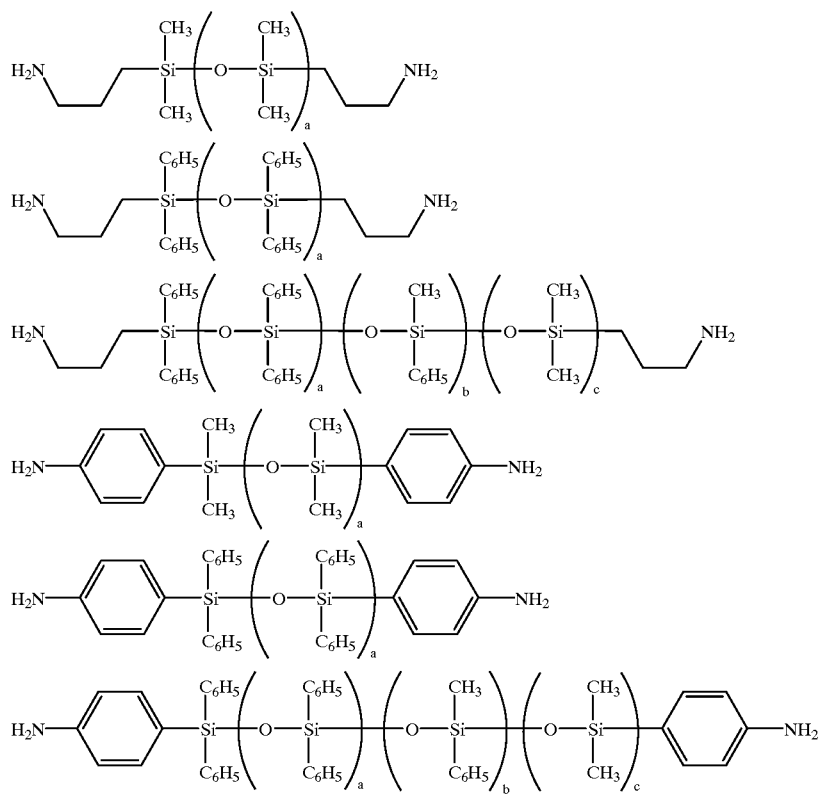

wherein a, b and c are an integer of 1 or more.

The tetracarboxylic dianhydride which may be used in this invention is represented by the formula [16] or [17].

These compounds may be specifically illustrated as follows:

3,3',4,4'-biphenyltetracarboxylic dianhydride, 2,2',3,3'-biphenyltetracarboxylic dianhydride, 2,3,3',4'-biphenyltetracarboxylic dianhydride, 3,3',4,4'-benzophenonetetracarboxylic dianhydride, 2,3,3',4'-benzophenonetetracarboxylic dianhydride, 2,2'3,3'-benzophenonetetracarboxylic dianhydride, bis(3,4-dicarboxyphenyl)ether dianhydride, bis(3,4-dicarboxyphenyl)sulfone dianhydride, bis(3,4-dicarboxyphenyl)methane dianhydride, 3,3',4,4'-hexafluoroisopropylidenediphthalic dianhydride, 3,3',4,4'-bicyclohexanetetracarboxylic dianhydride, bis(3,4-dicarboxycyclohexyl)ether dianhydride, bis(3,4-dicarboxycyclohexyl)sulfone dianhydride, bis( 3,3-dicarboyycyclohexyl)methane dianhydride, and the like. These compounds may include isomers thereof and a mixture of these isomers may be similarly used. A combination of two or more of these compounds may also be used. The tetracarboxylic dianhydride which may be used in this invention are not particularly limited to the above-mentioned compounds.

An aminosilicone compound represented by the formula [18] may be used, if necessary, in the polyimide, the liquid crystal aligning film and the liquid crystal display device of this invention.

[18]

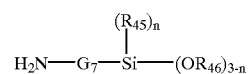

In the formula [18], $G_7$ is an alkylene group of 2–10 carbon atoms or a phenylene group, $R_{45}$ is an alkyl group of 1–10 carbon atoms, an alkenyl group of 2–10 carbon atoms or a phenyl group, $R_{46}$ is an alkyl group of 1–10 carbon atoms, an alkenyl group of 2–12 carbon atoms, a phenyl group or an alkoxyalkyl group of 2–10 carbon atoms, and n is an integer of 1–3.

Specific chemical names thereof may be mentioned below:

3-aminopropyltrimethoxysilane,
3-aminopropyltriethoxysilane,
3-aminopropylmethydimethoxysilane,
3-aminopropylmethydiethoxysilane, 3-aminopropyltris(2-methoxyethoxy)silane,
2-aminoethyltrimethoxysilane,
2-aminoethyltriethoxysilane,
2-aminoethylmethyldimethoxy-silane,
2-aminoethylmethyldiethoxysilane,
4-aminobutyltrimethoxysilane,
4-aminophenyltrimethoxysilane,
4-aminophenyltriethoxysilane,
4-aminophenylmethyldimethoxysilane,
4-aminophenylmethyldiethoxysilane,
4-aminophenyltris(2-methoxyethoxy)silane, 3-(4-aminophenyl)propyltrimethoxysilane, 3-(4-aminophenyl)propyltriethoxysilane,
3-aminophenyltrimethoxysilane,
3-aminophenyltriethoxysilane, 3-(4-aminophenyl)

propylmethyldimethoxysilane, 3-(4-aminophenyl) propylmethyldiethoxysilane, 3-aminophenylmethyldimethoxysilane, 3-aminophenylmethyldiethoxysilane, etc.

The said amino compound, diamine, tetracarboxylic dianhydride and diaminosilicone compound may be reacted with the acid anhydride group and the amino group in the presence of a publicly known solvent such as N-methyl-2-pyrrolidone (NMP) according to a publicly known method to afford the polyamic acid or the polyimide precursor of this invention.

In this reaction, the diamino compound represented by the formula [1] may preferably comprise 10 molar percent or more, and more preferably 50% or more, of the total amine. If the amount is reduced, the photosensitivity is lowered, whereby anisotropy by a polarized light would hardly develop. The aminosilicone compound may comprise preferably 30 molar percent or less, and more preferably 10% or less, of the total starting materials. These starting materials may be random-polymerized, block-polymerized or admixed with polymers (co)polymerized at a different composition. In the case where a tetracarboxylic dianhydride having an asymmetric configuration, the linked form of the said acid to the diamine is not necessarily in a given direction and the head-to-tail structure and the head-to-head structure may be intermingled. A polyimide composed of a plurality of tetracarboxylic dianhydrides or a plurality of the diamines may also be used.

In the compound represented by the said formula [1] and the structural unit represented by the formula [2], a length of the spacer $G_3$ may be preferably that of 0–12 carbon atoms, and more preferably that of 0–6. If the number of carbon atoms is more than 12, the structure has such an inferior heat resistance that the heat stability of the photocrosslinked film would be adversely affected.

In the formulae [1] and [2], the number m of the benzene rings to be substituted at the α-position of the side chain imido ring is preferably 1–2. If the ring number is more than the said range, the substituent will be so rigid that the solubility or coating property of the resulting polyamic acid may extremely decrease or there may be a risk of inhibiting the photoreaction because of steric hindrance.

The substituents X and Y in the formulae [1] and [2] may include the following atoms or functional groups, but they are not necessarily intended to be limited thereto. More specifically, they may include the atoms or cyclic substituents such as a hydrogen atom, a fluorine atom, a chlorine atom, a cyano group, a nitro group, a cyclopropyl group, a cyclobutyl group, a cyclopentyl group, a methylcyclopropyl group, an ethylcyclopropyl group, a propylcyclopropyl group, a n-butylcyclopropyl group, a methylcyclobutyl group, an ethylcyclobutyl group, a propylcyclobutyl group, a n-butylcyclobutyl group, a methylcyclopentyl group, an ethylcyclopentyl group, a propylcyclopentyl group, and a n-butylcyclopentyl group.

The alkyl group may include a methyl group, an ethyl group, a n-propyl group, an isopropyl group, a n-butyl group, an isobutyl group, a sec-butyl group, a t-butyl group, a n-pentyl group, an isopentyl group, a neo-pentyl group, a t-pentyl group, a n-hexyl group, an isohexyl group, a heptyl group, an octyl group, a nonyl group, a decyl group, an undecyl group, a dodecyl group, etc.

The haloalkyl group may include a trifluoromethyl group, a trichloromethyl group, a tribromomethyl group, a triiodomethyl group, a pentafluoroethyl group, a pentachloroethyl group, a pentabromoethyl group, a pentaiodoethyl group, a 1,1,1-trichloroethyl group, a 1,1,1-trifluoroethyl group, a 1,1,1-tribromoethyl group, a 1,1,1-triiodoethyl group, a heptafluoropropyl group, a heptachloropropyl group, a heptabromopropyl group, a heptaiodopropyl group, a 1,1,1-trifluoropropyl group, a 1,1,1-trichloropropyl group, a 1,1,1-tribromopropyl group, a 1,1,1-triiodopropyl group, a nonafluorobutyl group, a nonachlorobutyl group, a nonabromobutyl group, a nonaiodobutyl group, a perfluoropentyl group, a perchloropentyl group, a perbromopentyl group, a perfluorohexyl group, a perchlorohexyl group, a perbromohexyl group, a periodohexyl group, a perfluoroheptyl group, a perchloroheptyl group, a perbromoheptyl group, a perfluorooctyl group, a perchlorooctyl group, a perbromooctyl group, a perfluorononyl group, a perchlorononyl group, a perbromononyl group, a perfluorodecyl group, a perchlorodecyl group, a perbromodecyl group, etc.

The alkoxy group or the haloalkoxy group may include a methoxy group, an ethoxy group, a n-propoxy group, an isopropoxy group, a n-butoxy group, an isobutoxy group, a sec-butoxy group, a t-butoxy group, a n-pentyloxy group, an isopentyloxy group, a neo-pentyloxy group, a t-pentyloxy group, a n-hexyloxy group, an isohexyloxy group, a heptyloxy group, an octyloxy group, a nonyloxy group, a decyloxy group, an undecyloxy group, a dodecyloxy group, a trifluoromethoxy group, a trichloromethoxy group, a tribromomethoxy group, a triiodomethoxy group, a pentafluoroethoxy group, a pentachloroethoxy group, a pentabromoethoxy group, a pentaiodoethoxy group, a 1,1,1-trichloroethoxy group, a 1,1,1-trifluoroethoxy group, a 1,1,1-tribromoethoxy group, a 1,1,1-triiodoethoxy group, a heptafluoropropoxy group, a heptachloropropoxy group, a heptabromopropoxy group, a heptaiodopropoxy group, a 1,1,1-trifluoropropoxy group, a 1,1,1-trichloropropoxy group, a 1,1,1-tribromopropoxy group, a 1,1,1-triiodopropoxy group, a nonafluorobutoxy group, a nonachlorobutoxy group, a nonabromobutoxy group, a nonaiodobutoxy group, a perfluoropentyloxy group, a perchloropentyloxy group, a perbromopentyloxy group, a perfluorohexyloxy group, a perchlorohexyloxy group, a perbromohexyloxy group, a periodohexyloxy group, a perfluoroheptyloxy group, a perchloroheptyloxy group, a perbromoheptyloxy group, a perfluorooctyloxy group, a perchlorooctyloxy group, a perbromooctyloxy group, a perfluorononyloxy group, a perchlorononyloxy group, a perbromononyloxy group, a perfluorodecyloxy group, a perchlorodecyloxy group, a perbromodecyloxy group, etc.

Of the said substituents, preferable are a hydrogen atom, a fluorine atom, a cyano group, a methyl group, an ethyl group, a n-propyl group, a n-butyl group, a n-pentyl group, a n-hexyl group, a heptyl group, an octyl group, a nonyl group, a decyl group, an undecyl group, a dodecyl group, a heptafluoropropyl group, a nonafluorobutyl group, a perfluoropentyl group, a perfluorohexyl group, a perfluoroheptyl group, a perfluorooctyl group, a perfluorononyl group, a perfluorodecyl group, a methoxy group, an ethoxy group, a n-propoxy group, a n-butoxy group, a n-pentyloxy group, a n-hexyloxy group, a heptyloxy group, an octyloxy group, a nonyloxy group, a decyloxy group, an undecyloxy group, a dodecyloxy group, a heptafluoropropoxy group, a nonafluorobutoxy group, a perfluoropentyloxy group, a perfluorohexyloxy group, a perfluoroheptyloxy group, a perfluorooctyloxy group, a perfluorononyloxy group, a perfluorodecyloxy group, etc. More preferable are a hydrogen atom, a fluorine atom, a cyano group, a n-propyl group, a n-butyl group, a n-pentyl group, a n-hexyl group, a heptyl group, an octyl group, a nonyl group, a decyl group, an undecyl group, a dodecyl group, a perfluorohexyl group, a perfluoroheptyl group, a perfluorooctyl group, a perfluorononyl group, a perfluorodecyl group, a n-hexyloxy group, a heptyloxy group, an octyloxy group, a nonyloxy group, a decyloxy group, an undecyloxy group, a dodecyloxy group, a perfluorohexyloxy group, a perfluoroheptyloxy group, a perfluorooctyloxy group, a perfluorononyloxy group and a perfluorodecyloxy group.

For the preparation of the polyimide used for the aligning film for liquid crystal display device according to this invention, preferable is a method wherein a solution of the polyamic acid having the structural units represented by the formulae [2] and [3] is coated over a substrate and dehydration reaction is effected by heat treatment at 150–300° C. to form a polyimide thin film over the substrate, or a method wherein the polyamic acid is chemically dehydrated using acetic anhydride and the like to obtain the polyimide and then a solution of the polyimide is coated over a substrate and dried to form a thin film.

The solvent used for the polyamic acid represented by the formulae [2] and [3], which is applied for the aligning film for liquid crystal display device according to this invention, may include any solvent which is conventionally used for an aligning film for liquid crystal display device. More specifically, it may include aprotic polar organic solvents which are good solvents for these polymeric compounds, such as N-methyl-2-pyrrolidone, dimethyl-imidozolidinone, N-methyl-caprolactam, N-methylpropionamide, N,N-dimethyl-acetamide, dimethyl sulfoxide, N,N-dimethylformamide, N,N-diethyl-formamide, diethylacetamide and y-butyllactone.

If necessary, other solvent systems having a lowered surface tension may be used for the purpose of improving coating property. Examples thereof are an alkyl lactate, 3-methyl or 3-methoxy-butanol, tetralin, isophorone, an ethylene glycol monoalkyl ether such as ethylene glycol monobutyl ether, a diethylene glycol monoalkyl ether such as diethylene glycol monoethyl ether, an ethylene glycol monoalkyl or phenylacetate, a triethylene glycol monoalkyl ether, a propylene glycol monoalkyl ether such as propylene glycol monobutyl ether, a dialkyl malonate such as diethyl malonate, and the like. Many of these are rather poor solvents as compared with the good solvents as mentioned hereinbefore.

As a method for coating a solution dissolved in the said solvent onto a substrate to form liquid crystal display device, any conventional methods can be employed. Coating may be performed, for example, by a spinner method, a printing method, a dipping method, a dropping method and the like.

The heat treatment required for drying of the solvent after coating with the said solution may be carried out by any similar method to the procedures conventionally employed for aligning films of liquid crystal display device. For example, the heat treatment in an oven, a hot plate, an infrared furnace and the like is feasible. After coating with the solution, it is preferable that the solvent is evaporated at a relatively lower temperature and that the heat treatment is then performed at a temperature of around 150–300° C., preferably 180–250° C. It is also possible to add a surfactant used for improving coating property or an antistatic agent used for preventing static electricity and the like. It is further possible to mix a silane coupling agent or a titanium coupling agent for improving adhesion to the substrate.

Subsequently, the polyimide thin film is provided with anisotropy over the film surface by the irradiation of a polarized ultraviolet light thereto. A wavelength of the light irradiated to an α,β-substituted maleimide group, which is the photosensitive group used for the present aligning film for liquid crystal display device, is preferably 200–410 nm, more preferably 310–380 nm. An exposure of the polarized ultraviolet lights is at 0.05–15.0 J/cm$^2$, preferably 0.1–10.0 J/cm$^2$, and more preferably 0.1–5.0 J/cm$^2$.

The substrate for a liquid crystal display device may be conventionally a substrate on which an electrode, or specifically, a transparent electrode such as ITO (indium oxide—tin oxide) or tin oxide is formed. An insulating film for preventing alkali elution of the substrate, or a protective film such as a color filter and a color filter overcoat may be further provided between the electrode and the substrate, and an insulating film or an overcoat film such as a color filter film may be further provided on the electrode. An active element such as a TFT (Thin-Film-Transistor) element and a MIM (Metal-Insulation-Metal) element may also be formed on the electrode. As these electrodes, undercoats and other constitutions within a liquid crystal cell, any conventional constitutions of a liquid crystal display device may be applied.

A liquid crystal device may be prepared by forming a cell using the substrate thus formed, injecting a liquid crystal and sealing an injection inlet. As the liquid crystal to be enclosed, a wide variety of liquid crystals may be used, such as conventional nematic liquid crystals, and liquid crystals with a dichroic dye incorporated.

Specific examples of the liquid crystal composition which may be preferably used in combination with the present aligning film in this invention are the compositions which contain at least one compound selected from the group consisting of the compounds of the formulae [5], [6] and [7].

Examples thereof are also the liquid crystal compositions which contain at least one compound selected from the group consisting of the compounds of the formulae [8] and [9].

Examples thereof are also the liquid crystal compositions which contain at least one compound selected from the group consisting of the compounds of the formulae [10], [11] and [12].

Examples thereof are also the liquid crystal compositions which contain at least one compound selected from the group consisting of the compounds of the formulae [5], [6] and [7] and as a second component at least one compound selected from the group consisting of the compounds of the formulae [13], [14] and [15].

Examples thereof are also the liquid crystal compositions which contain at least one compound selected from the group consisting of the compounds of the formulae [8] and [9] and as a second component at least one compound selected from the group consisting of the compounds of the formulae [13], [14] and [15].

Examples thereof are also the liquid crystal compositions which contain at least one compound selected from the group consisting of the compounds ofrthe formulae [10], [11] and [12] and as a second component at least one compound selected from the group consisting of the compounds of the formulae [13], [14] and [15].

Moreover, examples thereof are the liquid crystal compositions which contain at least one compound selected from the group consisting of the compounds of the formulae [5], [6] and [7], as a second component at least one compound selected from the group consisting of the compounds of the formulae [8] and [9] and as a third component at least one compound selected from the group consisting of the compounds of the formulae [13], [14] and [15].

The said liquid crystal compositions can further include one or more of optically active compounds.

As the compounds of the formulae [5]–[7], the following compounds of the formulae (5-1) to (7-53) may be preferably mentioned.

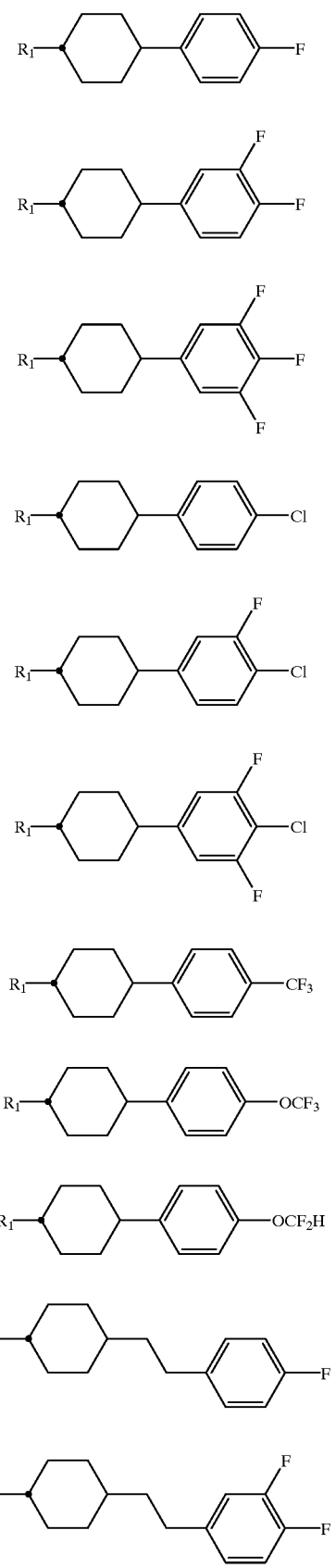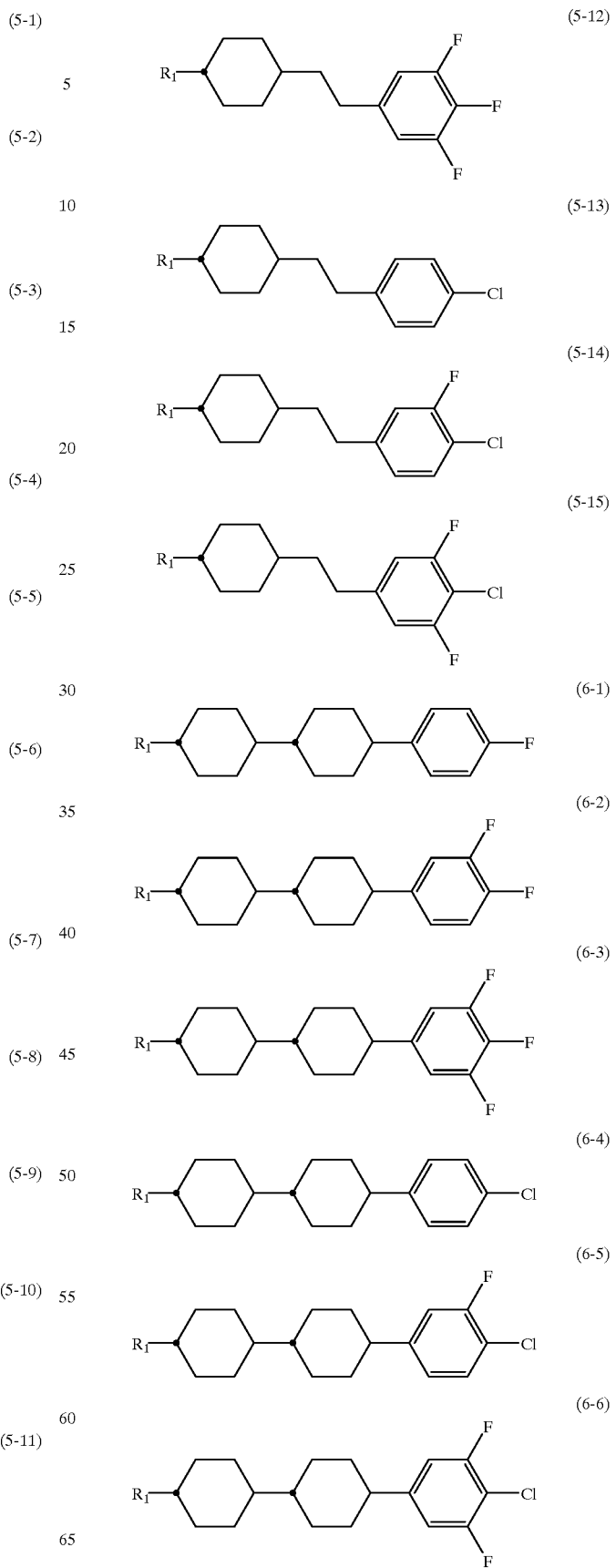

(6-7)
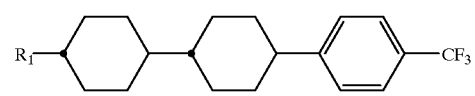
(6-8)
(6-9)
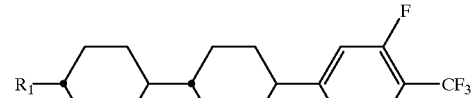
(6-10)
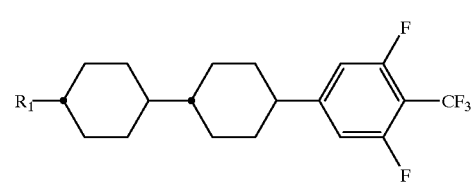
(6-11)
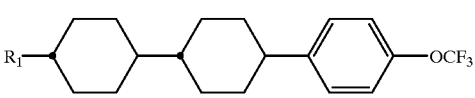
(6-12)
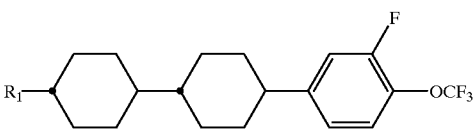
(6-13)
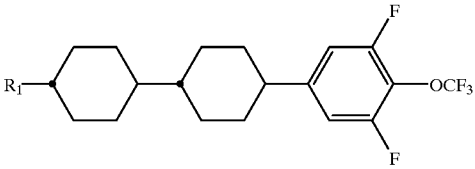
(6-14)
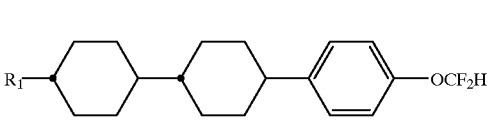
(6-15)
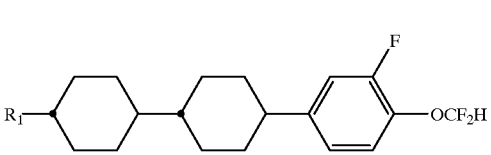
(6-16)
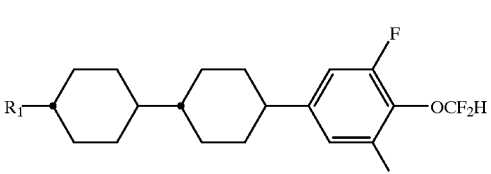
(6-17)
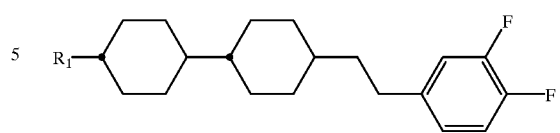
(6-18)
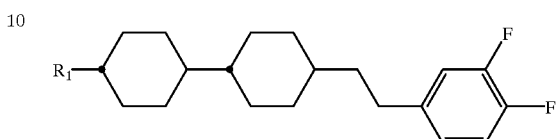
(6-19)
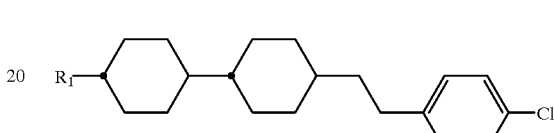
(6-20)
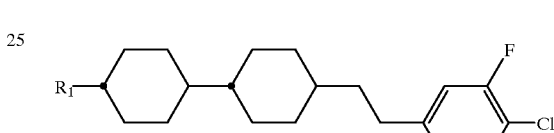
(6-21)
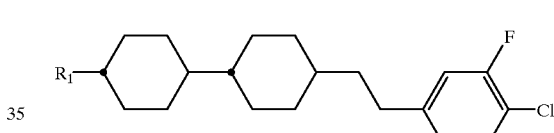
(6-22)
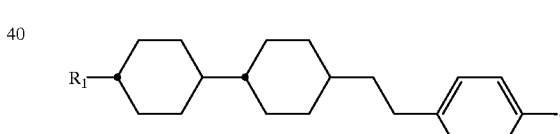
(6-23)
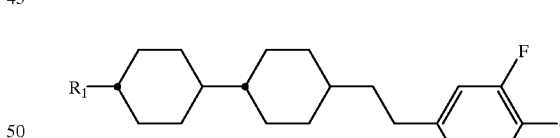
(6-24)
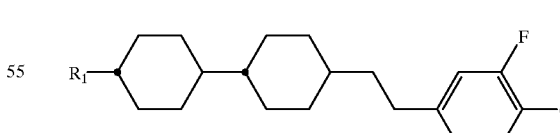
(6-25)
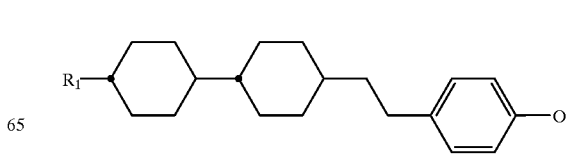

(6-26)
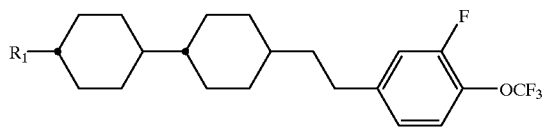
(6-27)
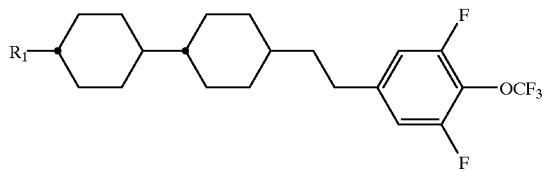
(6-28)
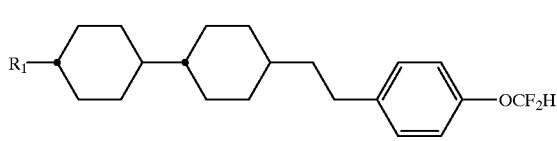
(6-29)
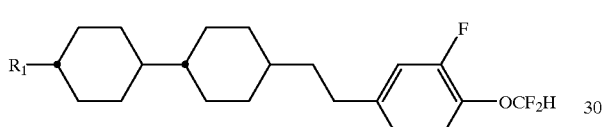
(6-30)
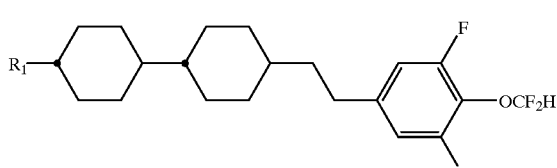
(6-31)
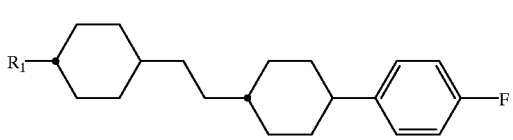
(6-32)
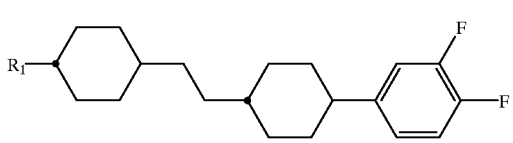
(6-33)
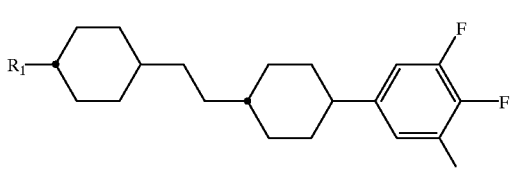
(6-34)
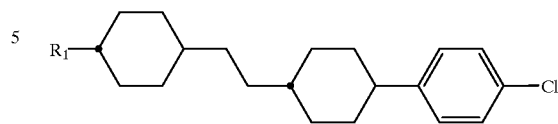
(6-35)
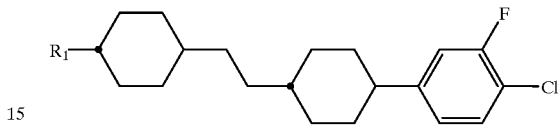
(6-36)
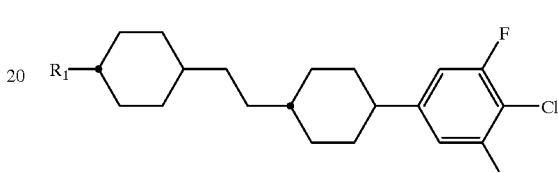
(6-37)
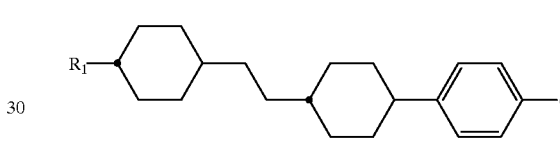
(6-38)
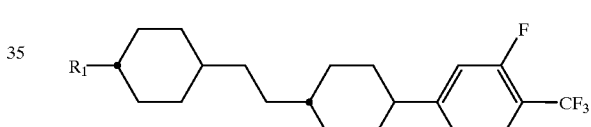
(6-39)
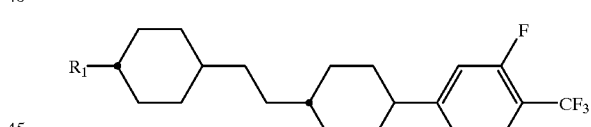
(6-40)
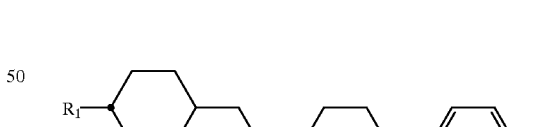
(6-41)
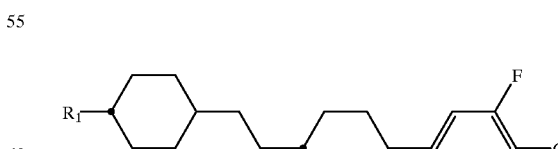

(6-42) 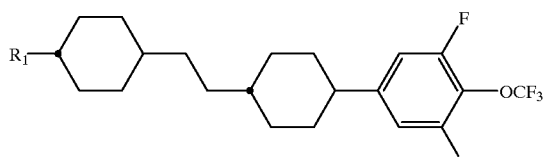
(6-43) 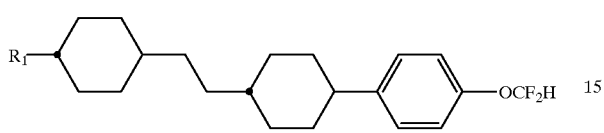
(6-44) 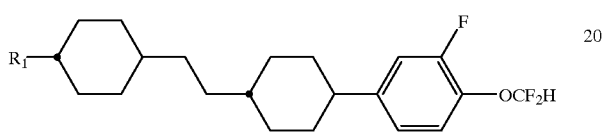
(6-45) 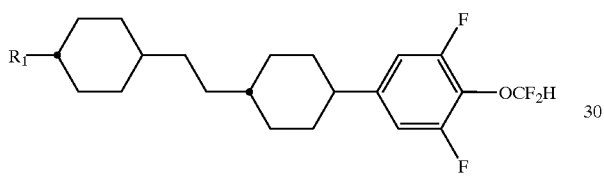
(6-46) 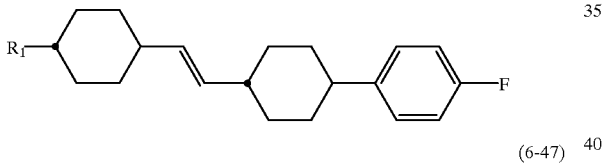
(6-47) 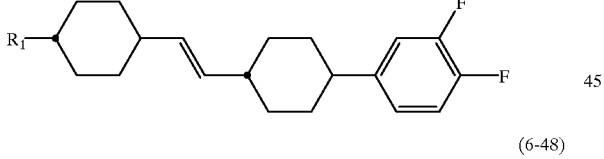
(6-48) 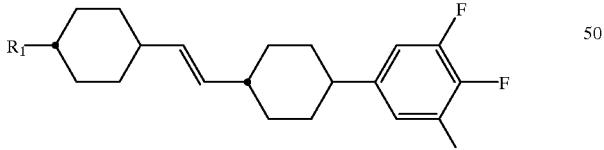
(7-1) 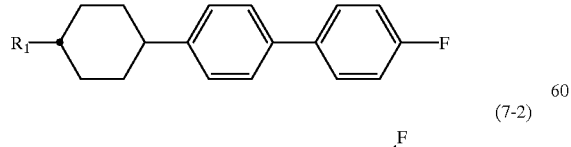
(7-2) 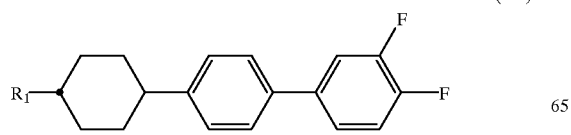
(7-3) 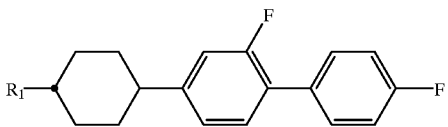
(7-4) 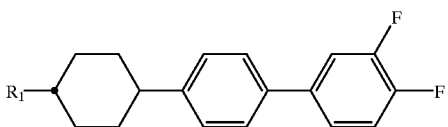
(7-5) 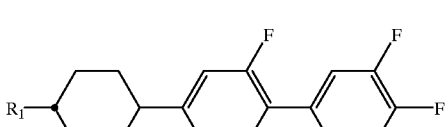
(7-6) 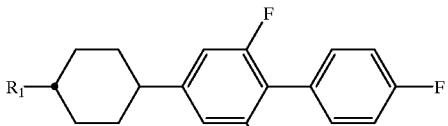
(7-7) 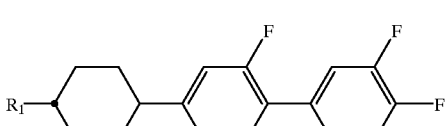
(7-8) 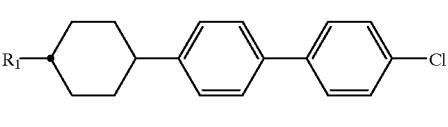
(7-9) 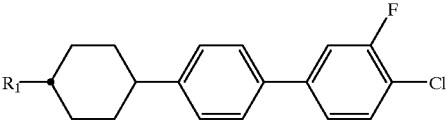
(7-10) 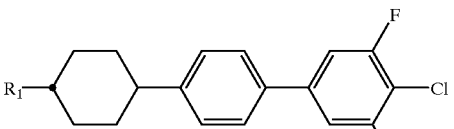
(7-11) 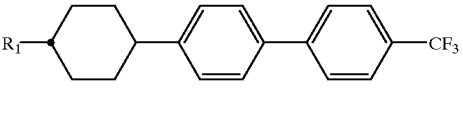
(7-12) 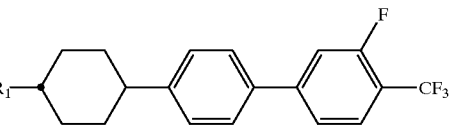

(7-13) 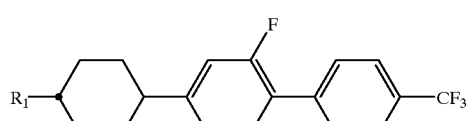
(7-14) 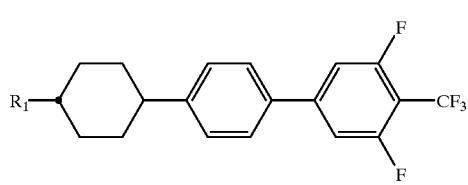
(7-15) 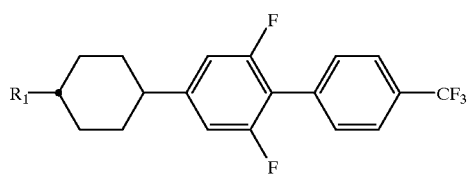
(7-16) 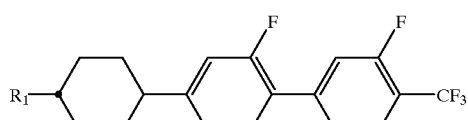
(7-17) 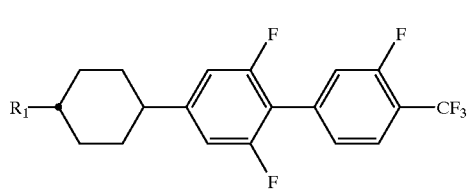
(7-18) 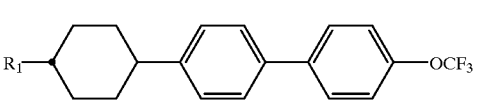
(7-19) 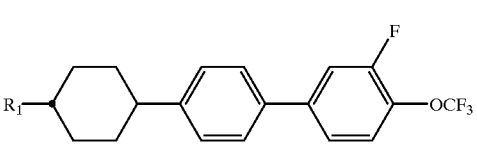
(7-20) 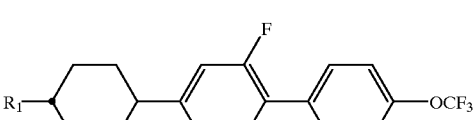
(7-21) 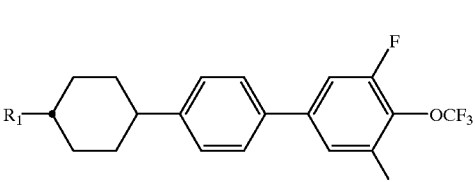
(7-22) 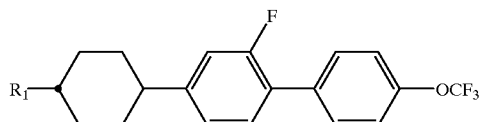
(7-23) 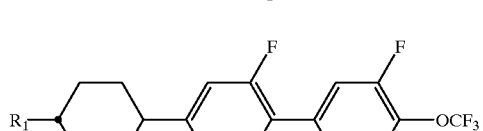
(7-24) 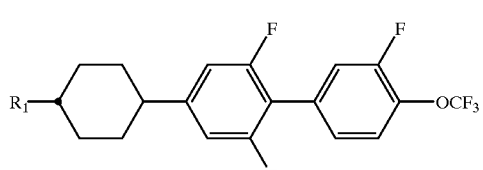
(7-25) 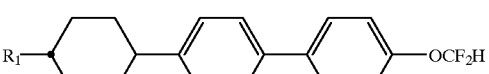
(7-26) 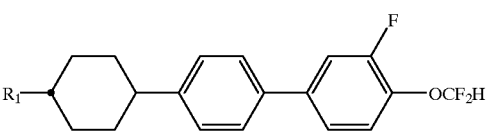
(7-27) 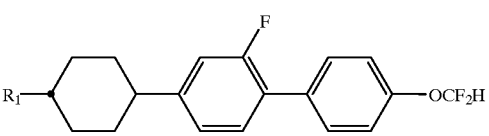
(7-28) 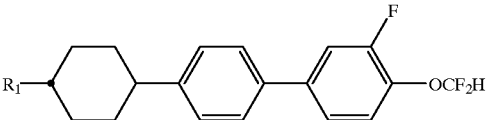
(7-29) 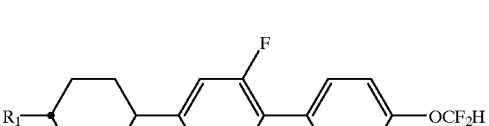
(7-29) 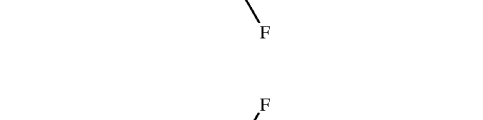

-continued (7-30) through (7-46): chemical structure diagrams of liquid crystal compounds.

(7-47)
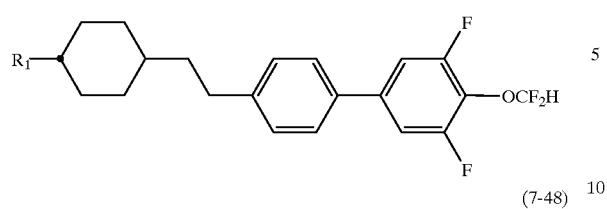

(7-48)
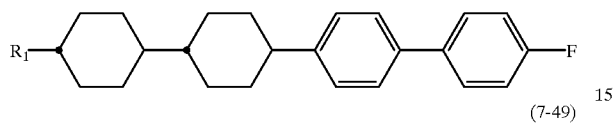

(7-49)
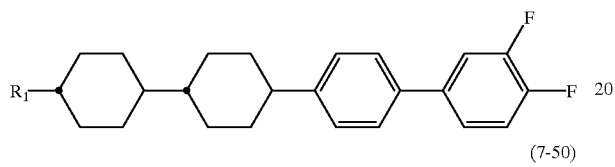

(7-50)
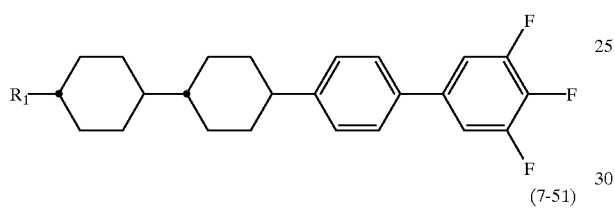

(7-51)
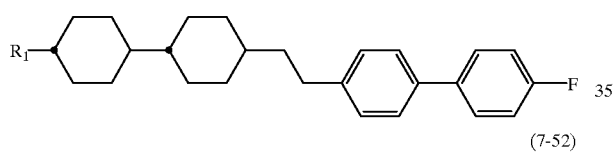

(7-52)
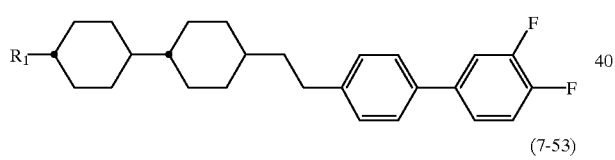

(7-53)
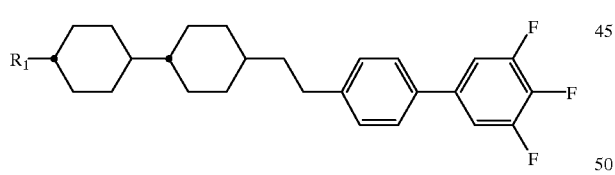

The compounds of the formulae [5]–[7] have a positive dielectric anisotropy and superior thermal and chemical stabilities, so that they are especially essential for the preparation of a liquid crystal composition for TFT which requires a high reliability such as a high voltage holding ratio and a large specific resistance.

As the compounds of the formulae [8] and [9], the following compounds of the formulae (8-1) to (9-3) may be preferably mentioned.

(8-1)
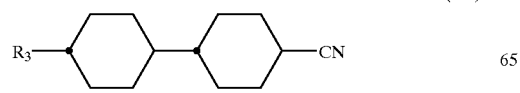

(8-2)
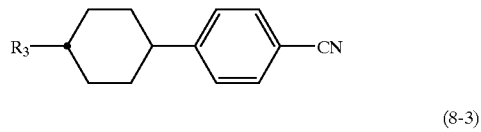

(8-3)
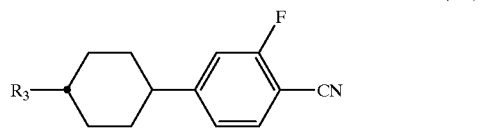

(8-4)

(8-5)
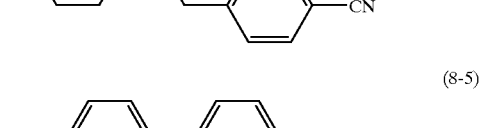

(8-6)
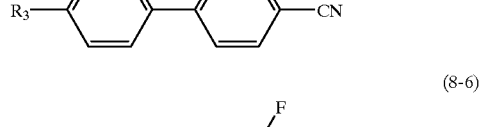

(8-7)
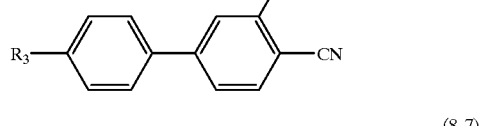

(8-8)
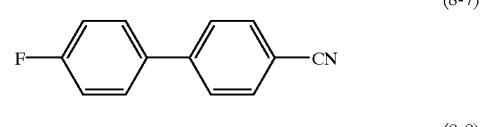

(8-9)
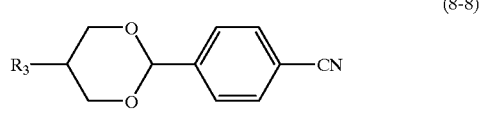

(8-10)
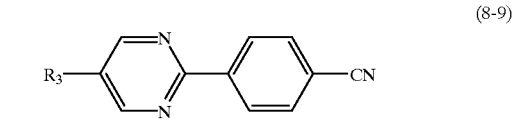

(8-11)
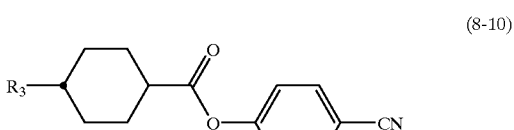

(8-12)
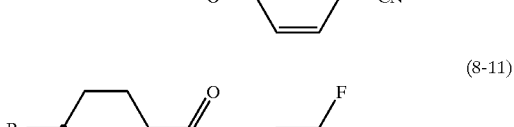

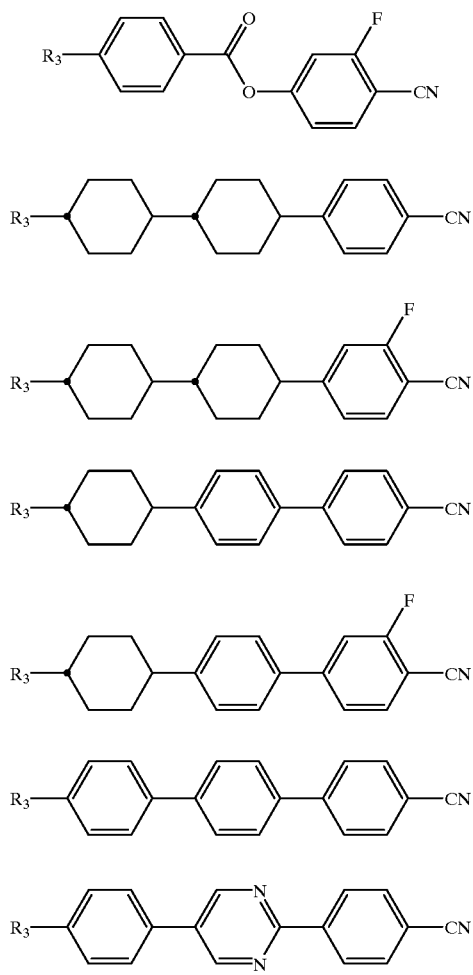

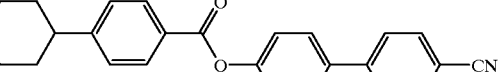

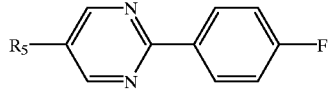

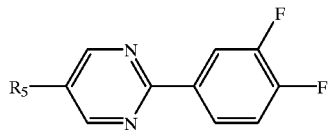

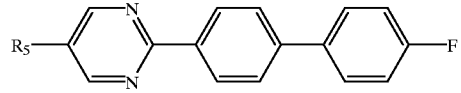

The compounds of the formulae [8] and [9] have a largely positive dielectric anisotropy, so that they are used especially for reducing a threshold voltage. They are also used for controlling a viscosity, controlling a refractive index anisotropy or broadening a nematic range such as raising a clear point. They are futher used for improving the steepness of a threshold voltage.

As the compounds of the formulae [10]–[12], the following compounds of the formulae (10-1) to (12-3) may be preferably mentioned.

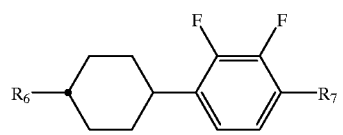

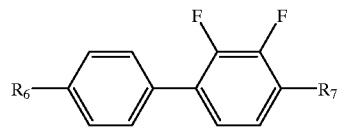

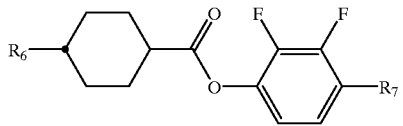

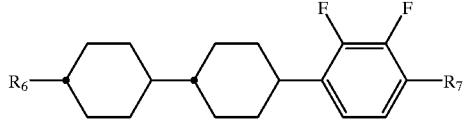

-continued (11-2)
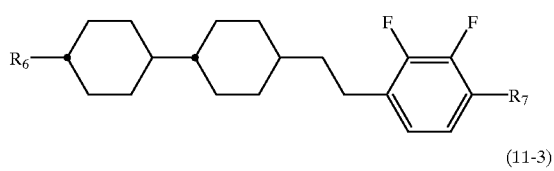

(11-3)
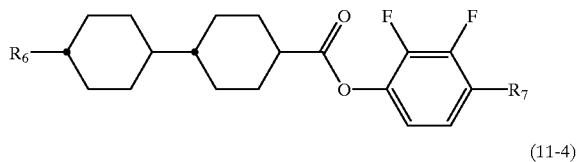

(11-4)
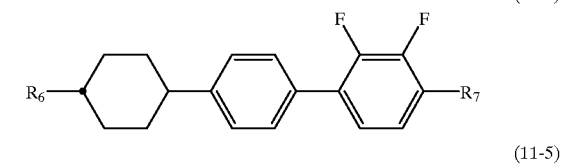

(11-5)
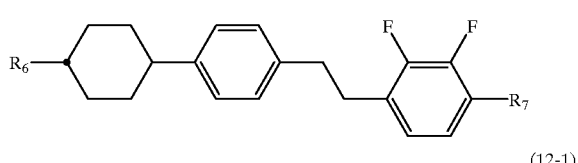

(12-1)
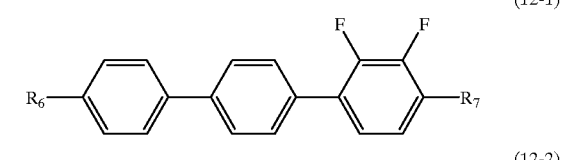

(12-2)
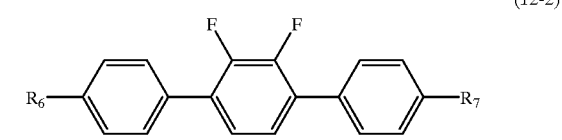

(12-3)
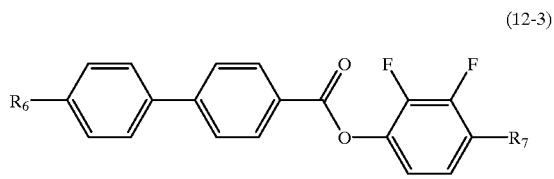

The compounds of the formulae [10]–[12] have a negative dielectric anisotropy. Since the compounds of the formula [10] are bicyclic compounds, they are used mainly for controlling a threshold voltage, controlling a viscosity or controlling a refractive index anisotropy. The compounds of the formula [11] are used for broadening a nematic range such as raising a clear point and also for controlling a refractive index anisotropy. The compounds of the formula [12] are used for controlling a refractive index anisotropy.

The compounds of the formulae [10]–[12] are used mainly for a liquid crystal composition having a negative dielectric anisotropy. If an amount of the compound of the formulae [10]–[12] is increased in a liquid crystal composition, a threshold voltage of the liquid crystal composition will be lower and a viscosity thereof will be higher. Accordingly, the compound may be preferably used in a less amount as far as the threshold voltage is within the required value. However, since an absolute value of dielectric anisotropy of the compounds of the formulae [10]–[12] is 5 or less, driving at a low voltage may not be performed in some cases if these compounds comprise less than 40% by weight.

In case of preparing a composition for TFT having a negative dielectric anisotropy, it is desirable that the compounds of the formulae [10]–[12] are used in the range of 40% by weight or more, and more preferably 50–95% by weight, based on the total weight of the liquid crystal composition. For the purpose of improving the steepness of a voltage-transmittance curve by controlling an elastic constant, the compounds of the formulae [10]–[12] may be blended with a composition having a positive dielectric anisotropy. In this case, it is preferred that the compound of the formulae [10]–[12] comprises 30% by weight or less of the liquid crystal composition.

As the compounds of the formulae [13]–[15], the compounds of the formulae (13-1) to (15-13) may be preferably mentioned.

(13-1)
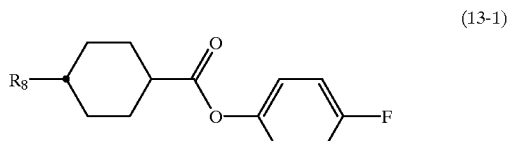

(13-2)
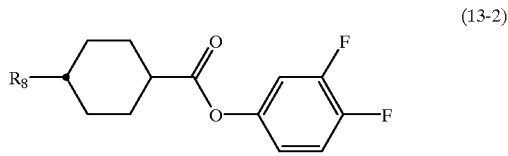

(13-3)
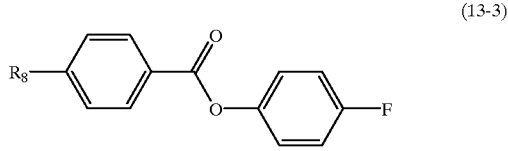

(13-4)
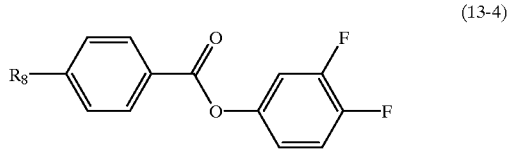

(13-5)
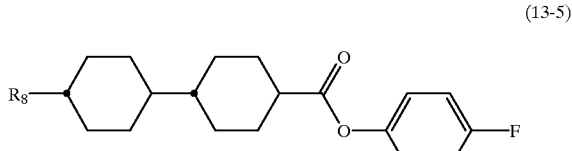

(13-6)
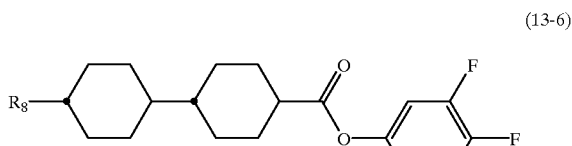

(13-7)
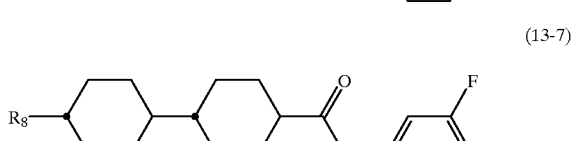

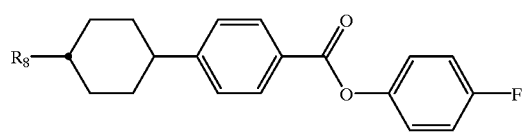
(13-8)
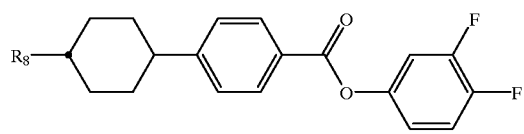
(13-9)
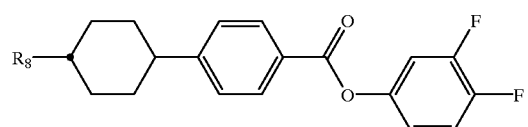
(13-10)
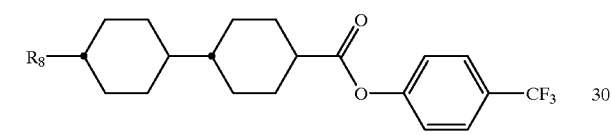
(13-11)
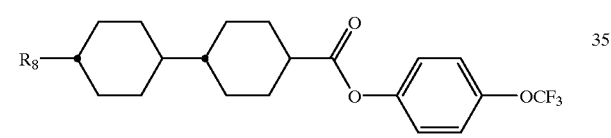
(13-12)
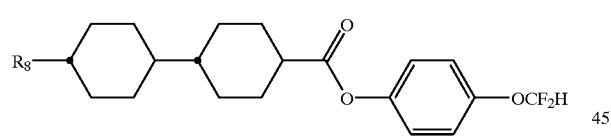
(13-13)
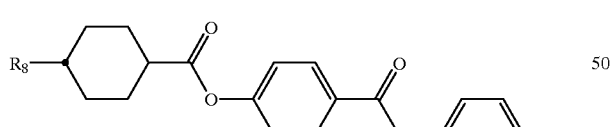
(13-14)
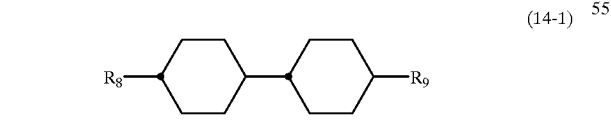
(14-1)
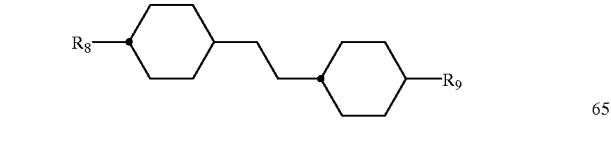
(14-2)
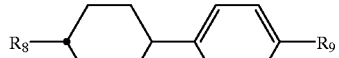
(14-3)
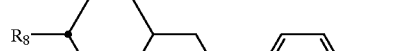
(14-4)
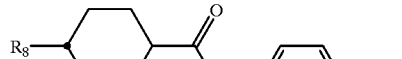
(14-5)
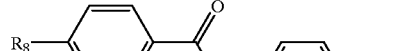
(14-6)
(14-7)
(15-1)
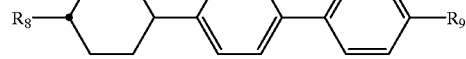
(15-2)
(15-3)
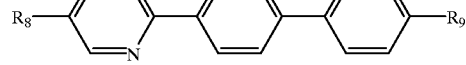
(15-4)
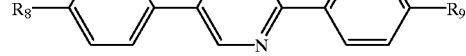
(15-5)
(15-6)

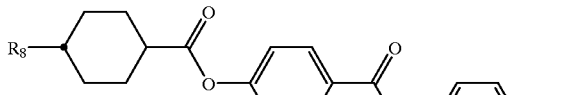 (15-7)

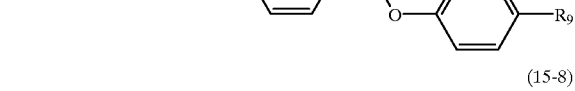 (15-8)

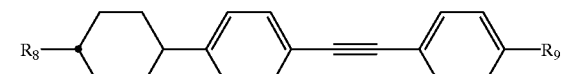 (15-9)

 (15-10)

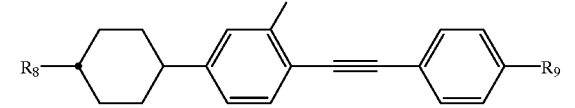 (15-11)

 (15-12)

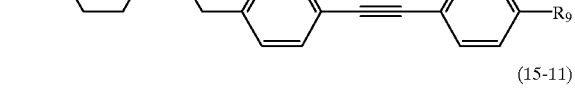 (15-13)

The compounds of the formulae [13]–[15] have a negative or weakly positive dielectric anisotropy. The compounds of the formula [13] are used mainly for reducing a viscosity or controlling a dielectric anisotropy. The compounds of the formula [15] are used for broadening a nematic range such as raising a clear point or for controlling a refractive index anisotropy.

Specific examples of the optically active compounds which may be used in this invention will be illustrated below.

Examples of the optically active compounds

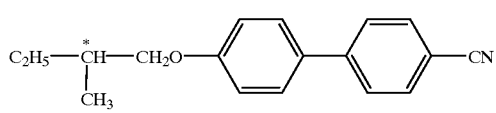

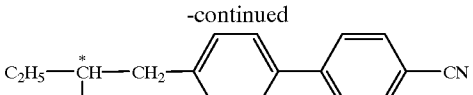

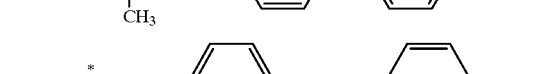

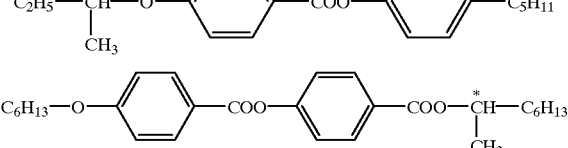

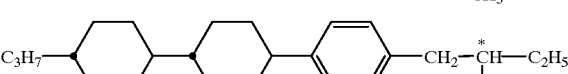

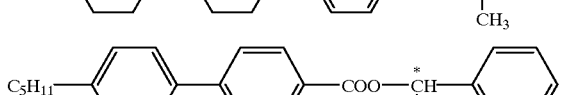

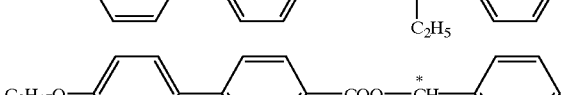

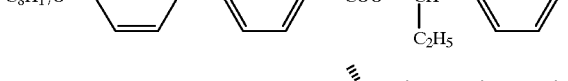

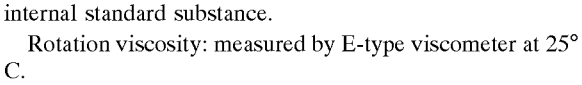

The liquid crystal display device of this invention is usually composed of a substrate, a voltage application means, a liquid crystal aligning film, a liquid crystal layer and so on. It is characterized by that it comprises an aligning film which can be rapidly photodimerized at a high sensitivity and is excellent in its thermal stability and shape retaining ability after crosslinked and has a good liquid crystal alignment, i.e., that it comprises the aligning film for liquid crystal display device of this invention.

BEST MODE FOR CARRYING OUT THE INVENTION

This invention will be explained in detail by way of the following examples, but this invention is in no way to be limited by these examples.

Physical properties of the compounds obtained by these examples were determined according to the following methods.

Melting point: measured at an elevated temperature by 5° C. per minute by means of a polarization microscope equipped with a hot stage (FP-82 manufactured by Metler Co., Inc.)

Nuclear Magnetic Resonance spectrum (NMR): EX-90A manufactured by JEOL LTD., using tetramethylsilane as an internal standard substance.

Rotation viscosity: measured by E-type viscometer at 25° C.

Logarithmic viscosity number: measured by Ubbelhode's viscometer in N-methyl-2-pyrrolidone at the polymer concentration of 0.5 g/dl at the temperature of 30±0.01° C.

EXAMPLE 1

1) Synthesis of a Polyimide Represented by the Following Structural Units:

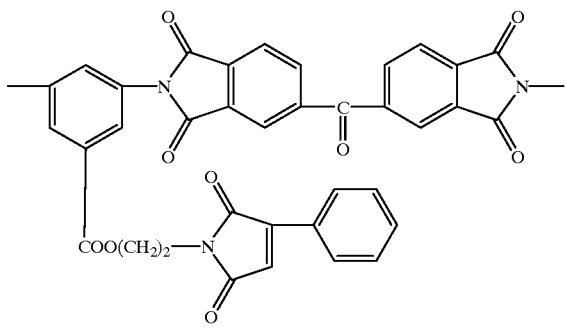

In a 1l three-necked flask equipped with a dropping funnel and a stirring means were placed 11.0 g of N-(2-hydroxyethyl)-α-phenylmaleimide and 500 ml of dioxane, and 7.70 ml of triethylamine was added at 0° C. under stirring. A dioxane solution of 11.5 g of 3,5-dinitrobenzoyl chloride was added dropwise thereto at 0° C. and stirring was continued at room temperature overnight. After completion of the reaction, 1l of water was added to the reaction solution and the resulting crystalline substance was collected by filtration. It was recrystallized twice from ethyl acetate to afford 6.10 g of N-(2-(3,5-dinitrobenzoyl)oxyethyl)-α-phenylmaleimide. This compound was subjected to reduction of a nitro group without any further purification. This compound had a melting point of 179.1–180.7° C.

In a 300 ml three-necked flask equipped with a dropping funnel and a stirring means were placed 8.22 g of N-(2-(3,5-dinitrobenzoyl)oxyethyl)-α-phenylmaleimide and 150 ml of dioxane, and 30.2 g of stannous chloride (dihydrate) was added at room temperature under stirring. Then, 30.2 g of conc. hydrochloric acid was added dropwise thereto, and thereafter, stirring was continued at room temperature for 3 hours. After completion of the reaction, a 2N aqueous solution of sodium hydroxide was added dropwise thereto until it was neutral, and the reaction solution was filtered with Celite. The filtrate was extracted twice with ethyl acetate, and the organic phase was washed three times with water and dried over anhydrous magnesium sulfate. After the drying agent was filtered off, the filtrate was concentrated under reduced pressure to afford a yellow solid. This solid was recrystallized twice from ethyl acetate to afford 6.42 g of N-(2-(3,5-diaminobenzoyl)oxyethyl)-α-phenylmaleimide.

This compound had the following melting point and NMR:

Melting point: 182–184° C.; $^1$H-NMR (90 MHz, DMSO-d$_6$: δ 3.82 (t, 2H), 4.39 (t, 2H), 4.90 (bs, 4H), 6.04 (t, 1H), 6.40 (d, 2H), 7.27 (s, 1H), 7.50–8.09 (m, 5H).

2) Polymerization Reaction

In a 100 ml three-necked flask were placed 3.514 g 25 of N-(2-(3,5-diaminobenzoyl)oxyethyl)-α-phenylmaleimide and 19.1 g of NMP and they were dissolved by stirring under a nitrogen stream at room temperature. Thereafter, the reaction solution was maintained at 10° C. and 1.611 g of 3,3',4,4'-benzophenonetetracarboxylic dianhydride was added thereto. The reaction was carried out at room temperature for 6 hours to afford a 15.0% by weight polymer solution. This polymer had a logarithmic viscosity number of 0.85 dl/g.

3) Formation of an Aligning Film of a Liquid Crystal Display Device by a Polarized Light Irradiation The polyamic acid solution as obtained in the above 2) was diluted to 5.0% by weight with a solvent of NMP/Butyl Cellosolve=1/1 and filtered through a filter of 0.1 μm to form a solution of a liquid crystal aligning agent. It was coated over an ITO glass substrate according to a rotational coating (a spinner method). After coating, heating at 230° C. for 60 minutes provided a thin film about 740 Å thick. The surface of the thin film was exposed to a linear polarized ultraviolet light with a wavelength of around 365 nm from an ultra-high pressure mercury lamp at 2.0 J/cm$^2$.

4) Preparation of a Liquid Crystal Cell and Assessment of Alignment

The substrates as obtained in the above 3) were laminated so as to produce a paralleled polarization direction of an ultraviolet light, which provided a liquid crystal cell having a liquid crystal layer 20 μm thick. Into the cell was injected the liquid crystal JC-5006 manufactured by Chisso Corporation and heat treatment was performed at 110° C. for 30 minutes. After the heat treatment, it was allowed to cool and the alignment of the liquid crystal was proved to be satisfactory.

EXAMPLE 2

Synthesis of a Polyimide Represented by the Following Structural Units:

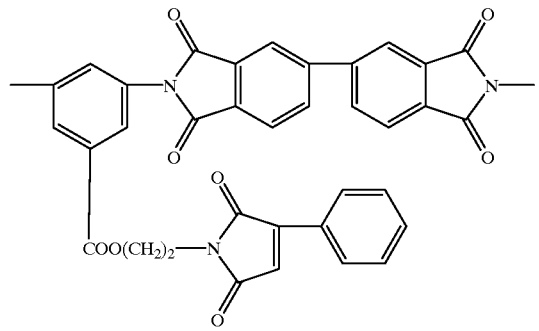

Synthesis of a polyamic acid was carried out in the entirely same manner as in Example 1 except that 3,3',4,4'-biphenyltetracarboxylic dianhydride was used as the tetracarboxylic dianhydride while a molar ratio of the tetracarboxylic dianhydride to the diamine was maintained at 1. The resulting polymer had a logarithmic viscosity number of 0.82 dl/g. The polymer was treated in the same manner as in Example 1, and an aligning film was prepared. The alignment of the liquid crystal was investigated and proved to be satisfactory.

EXAMPLE 3

1) Synthesis of a Polyimide Represented by the Following Structural Units:

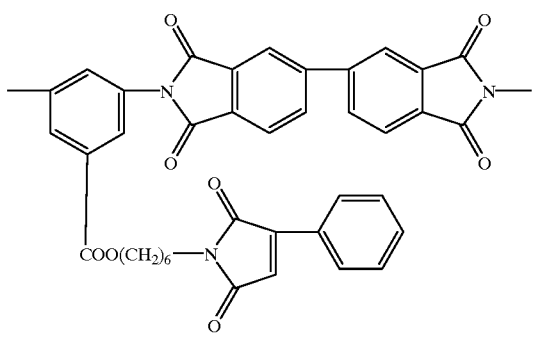

Synthesis was carried out in the same manner as in Example 1 except that N-(6-hydroxyhexyl)-α-phenylmaleimide was used instead of the N-(2-hydroxyethyl)-α-phenylmaleimide as used in 1) of Example 1, to afford N-(6-(3,5-diaminobenzoyl)oxyhexyl)-a-phenylmaleimide. This compound had the following melting point and NMR:

Melting point: 106.8–108.9° C.; $^1$H-NMR (90 MHz, CDCl$_3$): δ1.26–1.84 (m, 8H), 3.51–3.76 (m, 6H), 4.24 (t, 2H), 6.16 (t, 1H), 6.71 (s, 1H), 6.78 (d, 2H), 7.41–7.97 (m, 5H).

2) Polymerization Reaction

A solution of a polyamic acid having a logarithmic viscosity number of 0.68 dl/g was obtained in the same manner as in Example 2 except that 4.076 g of N-(6-(3,5-diaminobenzoyl)oxyhexyl)-α-phenylmaleimide was used as the diamine component while a molar ratio of the tetracarboxylic dianhydride to the diamine was maintained at 1.

3) Polarized Light Irradiation, Formation of Cell and Assessment of Alignment

In the same manner as in Example 1, the alignment of the liquid crystal was proved to be satisfactory.

EXAMPLE 4

Synthesis of a Polyimide Represented by the Following Structural Units:

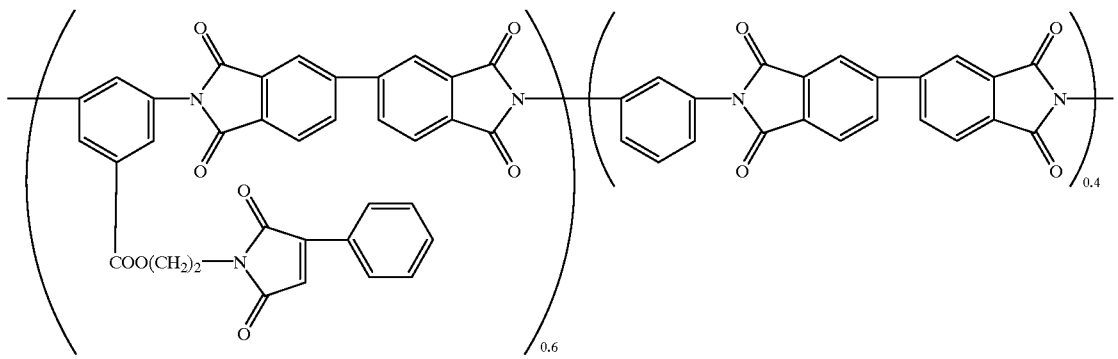

A polyamic acid was synthesized in the same manner as in Example 1 except that the molar ratio 3,3',4,4'-biphenyltetracarboxylic dianhydride/N-(2-(3,5-diaminobenzoyl)oxyethyl)-α-phenylmaleimide/metaphenylenediamine=1/0.6/0.4 was used as the ratio of the tetracarboxylic dianhydride to the diamine, to obtain a polymer solution having a logarithmic viscosity number of 1.3 dl/g. An aligning film was similarly prepared using this polymer and the alignment of the liquid crystal was investigated and proved to be satisfactory.

EXAMPLE 5

1) Synthesis of a Polyimide Represented by the Following Structural Units:

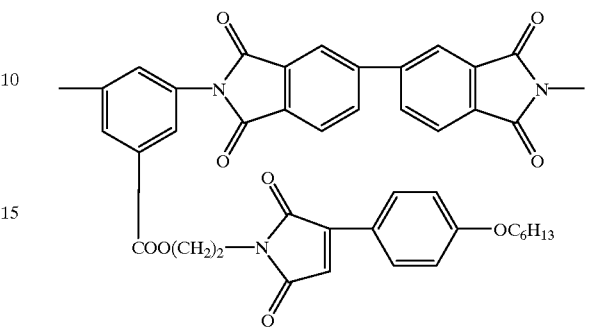

Synthesis was carried out in the same manner as in Example 1 except that N-(2-hydroxyethyl)-α-(4-hexyloxy)phenylmaleimide was used instead of the N-(2-hydroxyethyl)-α-phenylmaleimide as used in 1) of Example 1, to afford N-(2-(3,5-diaminobenzoyl)oxyethyl)-α-(4-hexyloxy)phenylmaleimide. This compound had the following melting point and NMR:

Melting point: 134.4–135.9° C.; $^1$H-NMP (90 MHz, CDCl$_3$) : δ0.906 (t, 3H), 1.23–1.87 (m, 8H), 3.62 (bs, 4H), 3.93–4.08 (m, 4H), 4.38 (t, 2H), 6.17 (t, 1H), 6.62 (d, 2H), 6.69 (s, 1H), 7.43 (ABq, 4H).

2) Polymerization Reaction

A solution of a polyamic acid having a logarithmic viscosity number of 0.59 dl/g was obtained in the same manner as in Example 2 except that 4.515 g of N-(6-(3,5-diaminobenzoyl)oxyhexyl)-α-(4-hexyloxy)phenylmaleimide was used as the diamine component while a molar ratio of the tetracarboxylic dianhydride to the diamine was maintained at 1.

3) Polarized Light Irradiation, Formation of Cell and Assessment of Alignment

In the same manner as in Example 1, the alignment of the liquid crystal was proved to be satisfactory.

EXAMPLE 6

1) Synthesis of a Polyimide Represented by the Following Structural Units:

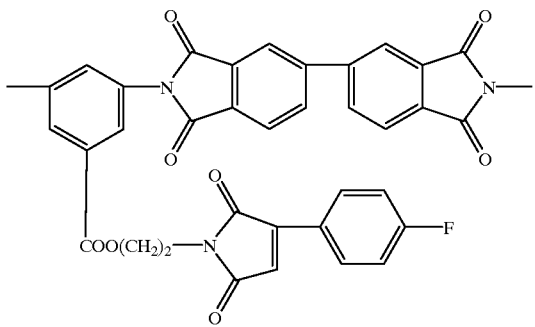

Synthesis was carried out in the same manner as in Example 1 except that N-(2-hydroxyethyl)-α-(4-fluorophenyl)maleimide was used instead of the N-(2-hydroxyethyl)-α-phenylmaleimide as used in 1) of Example 1, to afford N-(2-(3,5-diaminobenzoyl)oxyethyl)-α-(4-fluorophenyl)maleimide. This compound had the following melting point and NMR:

Melting point: 154.4–156.1° C.; $^1$H-NMR (90 MHz, DMSO-$d_6$): δ3.99 (t, 2H), 4.37 (t, 2H), 4.91 (bs, 4H), 6.07 (t, 1H), 6.40 (d, 2H), 7.24 (s, 1H), 7.32–8.25 (m, 4H).

2) Polymerization Reaction

A solution of a polyamic acid having a logarithmic viscosity number of 0.85 dl/g was obtained in the same manner as in Example 2 except that 3.694 g of N-(6-(3,5-diaminobenzoyl)oxyhexyl)-α-(4-fluorophenyl)maleimide was used as to the diamine component while a molar ratio of the tetracarboxylic dianhydride to the diamine was maintained at 1.

3) Polarized Light Irradiation, Formation of Cell and Assessment of Alignment

In the same manner as in Example 1, the alignment of the liquid crystal was proved to be satisfactory.

EXAMPLE 7

1) Synthesis of a Polyimide Represented by the Following Structural Units:

5.0 ml of phosphorus trichloride was further added. After stirring for another one hour, the reaction solution was poured into ice-water and the crystals thus separated were collected by filtration. The crude crystal was dried under reduced pressure and then recrystallized from n-theptane/ethyl acetate to afford 12.1 g of N-chloromethyl-α-phenylmaleimide.

In a 500 ml three-necked flask equipped with a stirring means and a condenser were placed 10.0 g of N-5 chloromethyl-α-phenylmaleimide and 200 ml of DMF, and dissolved at room temperature with stirring. Further, 10.3 g of 2,4-dinitrophenol sodium salt was added and the reaction was carried out at 80° C. for 12 hours. After completion of the reaction, the reaction solution was poured into a large volume of water and extracted three times with ethyl acetate. The organic layer was washed three times with water and dried over anhydrous magnesium sulfate. The drying agent was separated by filtration and the organic layer was concentrated under reduced pressure. The resulting yellow crystal was collected by filtration with n-heptane to afford N-(2,4-dinitrophenyl)oxymethyl-α-phenylmaleimide. This compound was used as such for the subsequent reaction.

Reduction reaction was carried out in the same manner as in Example 1 except that N-(2,4-dinitrophenyl)oxymethyl-α-phenylmaleimide was used instead of the N-(2-(3,5-dinitrobenzoyl)oxyethyl)-α-phenylmaleimide as used in 1) of Example 1, to afford 6.40 g of N-(2,4-diaminophenyl)oxymethyl-α-phenylmaleimide. This compound had the following melting point and NMR:

Melting point: 183.7–185.6° C. $^1$H-NMR (90 MHz, DMSO-$d_6$): δ3.37 (bs, 4H), 5.19 (s, 2H), 7.14 (s, 1H), 7.25–8.00 (m, 8H). ps 2) Polymerization Reaction A solution of a polyamic acid having a logarithmic viscosity number of 0.44 dl/g was obtained in the same manner as in Example 2 except that 3.093 g of N-(2,4-diaminophenyl)oxymethyl-α-phenylmaleimide was used as the diamine component while a molar ratio of the tetracarboxylic dianhydride to the diamine was maintained at 1.

3) Polarized Light Irradiation, Formation of Cell and Assessment of Alignment

In the same manner as in Example 1, the alignment of the liquid crystal was proved to be satisfactory.

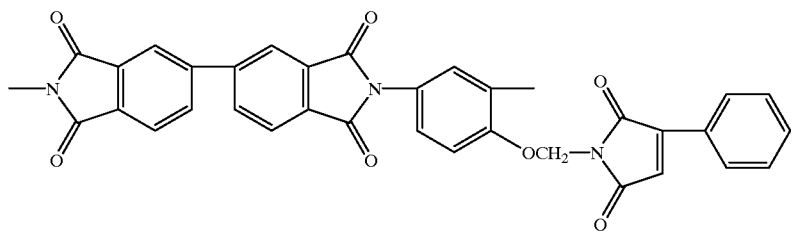

In 200 ml of acetone was suspended 20.3 g of N-hydroxymethyl-α-phenylmaleimide and then 4.6 ml of phosphorus trichloride was added in one portion at room temperature. After the mixture was stirred for 30 minutes,

EXAMPLE 8

1) Synthesis of a Polyimide Represented by the Following Structural Units:

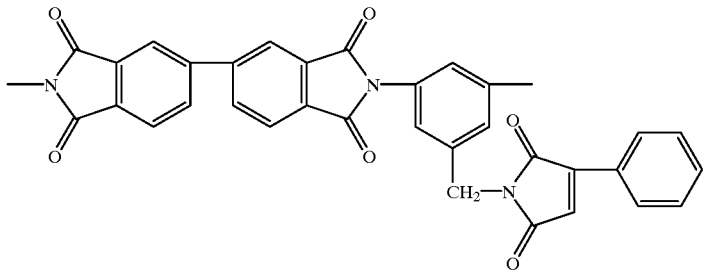

In a 500 ml three-necked flask equipped with a stirring means and a dropping funnel were placed 7.92 g of 3,5-dinitrobenzyl alcohol, 6.90 g of α-phenylmaleimide and 11.5 g of triphenylphosphine, and the mixture was dissolved in 200 ml of THF with stirring. To the solution was added dropwise 20.9 g of diethyl azodicarboxylate (as a 40% toluene solution) at 0° C. or lower. After the dropwise addition, the temperature was allowed to rise to room temperature and stirring was continued for 24 hours. The reaction solution was poured into water and extracted three times with ethyl acetate. The organic layer was washed three times with water and dried over anhydrous magnesium sulfate. The drying agent was separated by filtration and the organic layer was concentrated under reduced pressure. The resulting pale yellow crystal was collected by filtration with n-heptane and recrystallized twice from ethyl acetate to afford 10.41 g of N-(3,5-dinitrophenyl)methyl-α-phenylmaleimide.

Reduction of the nitro group was carried out in the same manner as in Example 1 except that N-(3,5-dinitrophenyl)methyl-α-phenylmaleimide was used instead of the N-(2-(3,5-dinitrobenzoyl)oxyethyl)-α-phenylmaleimide as used in 1) of Example 1. The subsequent purification by a silica gel column (n-heptane/ethyl acetate=1/1) gave 3.14 g of N-(2,4-diaminophenyl)-methyl-α-phenylmaleimide as a yellow oily substance. This compound had the following NMR:

$^1$H-NMR (90 MHz, CDCl$_3$): δ3.56 (bs, 4H), 5.01 (s, 2H), 5.96 (d, 1H), 6.09 (d, 2H), 6.35 (s, 1H), 7.42 (s, 5H).

2) Polymerization Reaction

A solution of a polyamic acid having a logarithmic viscosity number of 0.68 dl/g was afforded in the same manner as in Example 2 except that 2.93 g of N-(3,5-diaminophenyl)methyl-α-phenylmaleimide was used as the diamine component while a molar ratio of the tetracarboxylic dianhydride to the diamine was maintained at 1.

3) Polarized Light Irradiation, Formation of Cell and Assessment of Alignment

In the same manner as in Example 1 except that an irradiation intensity of ultraviolet light was changed to 0.1 J/cm$^2$, the alignment of the liquid crystal was proved to be satisfactory.

EXAMPLE 9

Using the same polyamic acid as in Example 2, liquid crystal cells were prepared in the same manner as in Example 2 except that the liquid crystal compositions (LA)–(LE) were used as those for TFT, and the alignment thereof was proved to be satisfactory. Formulations of the liquid crystal compositions (LA)–(LE) as used herein will be shown below.

Liquid Crystal Composition (LA)

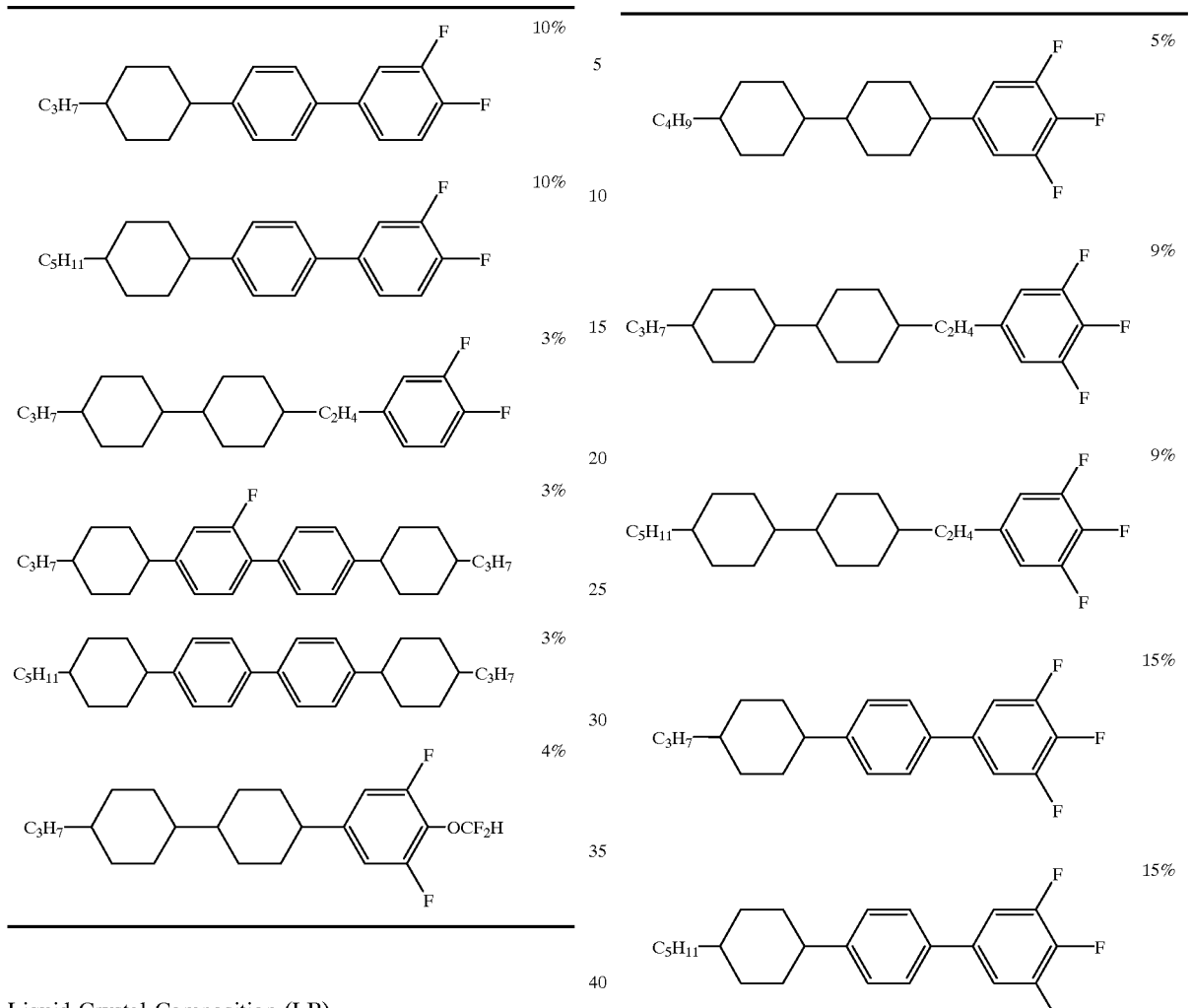
Liquid Crystal Composition (LB)
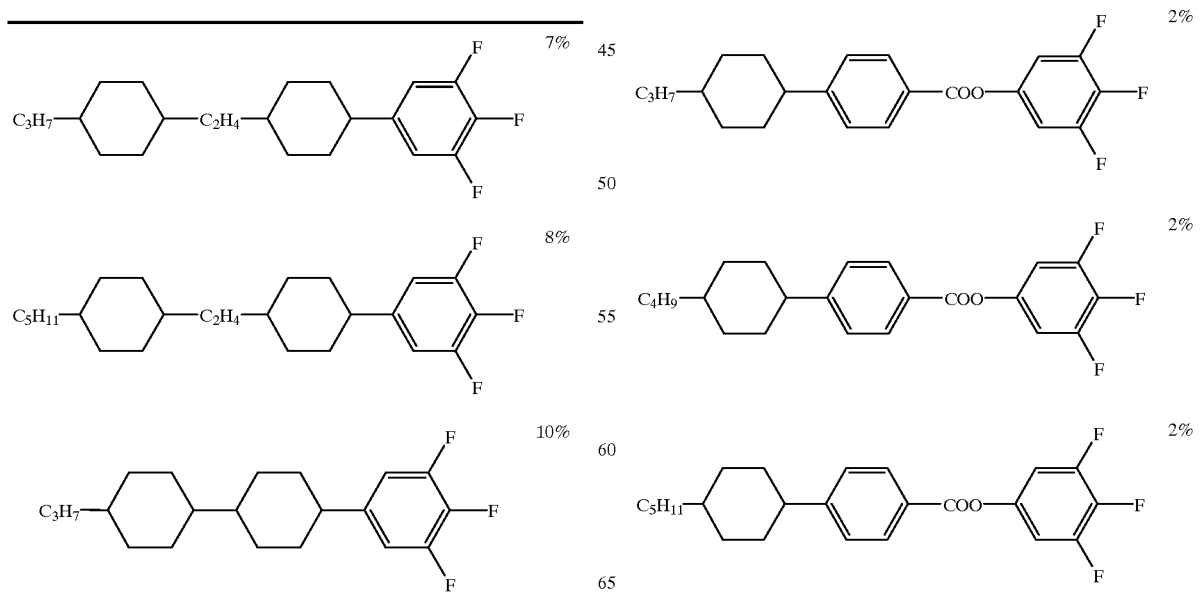

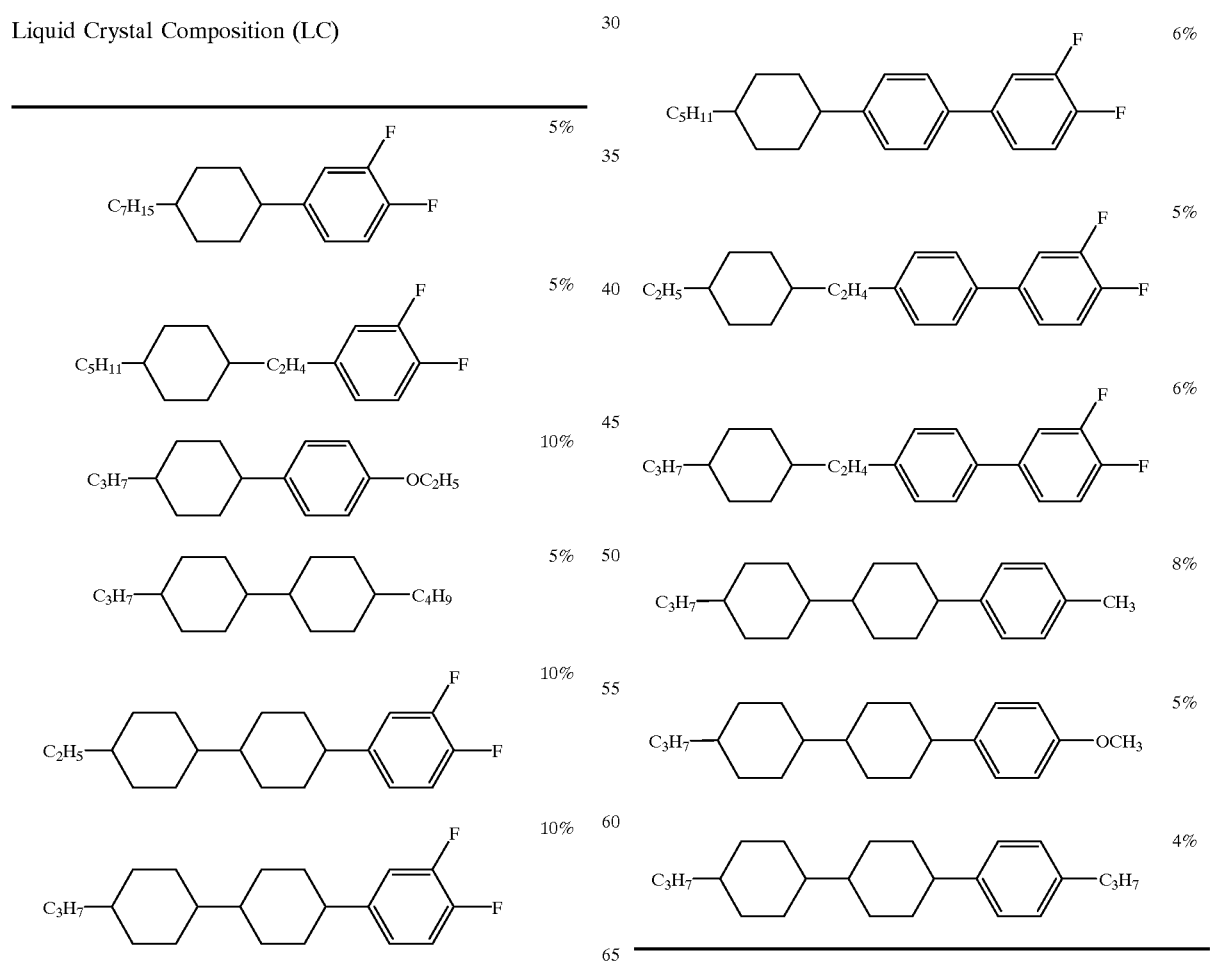

Liquid Crystal Composition (LD)
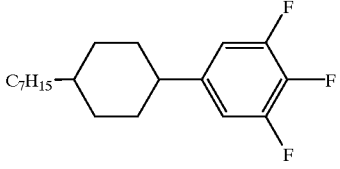 5%
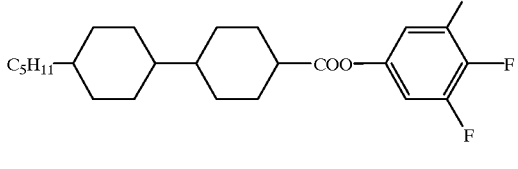 12%
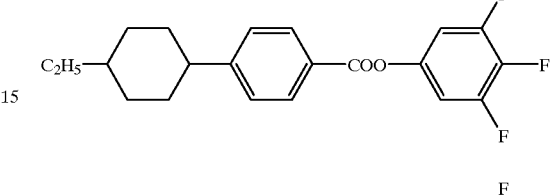 10%
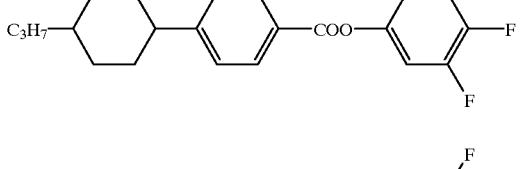 10%
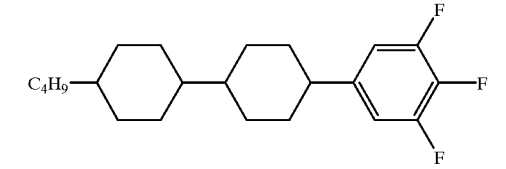 5%
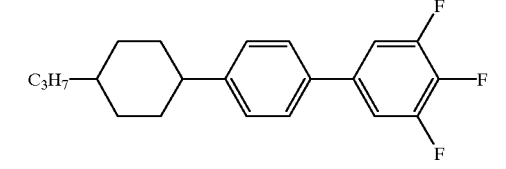 10%
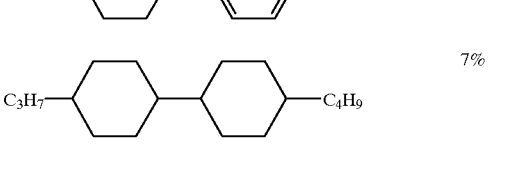 10%
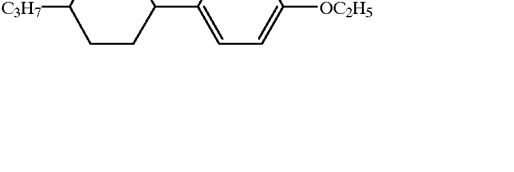 3%
-continued
 3%
3%
5%
3%
15%
6%
Liquid Crystal Composition (LE)
12%
7%
20%

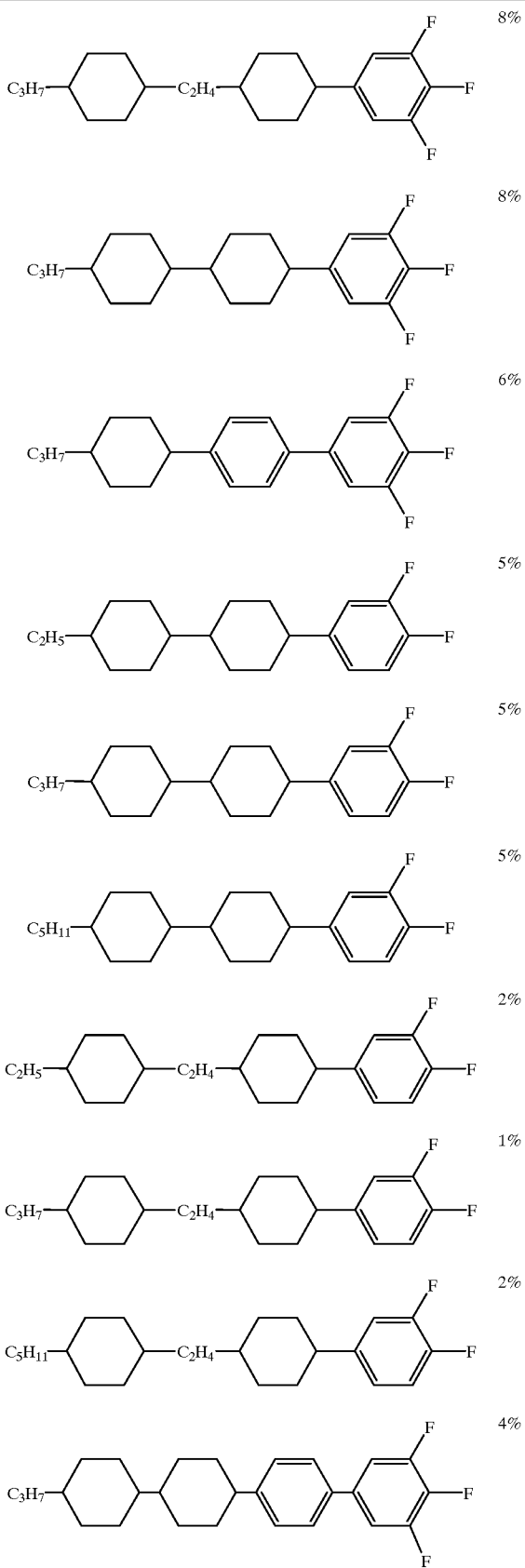

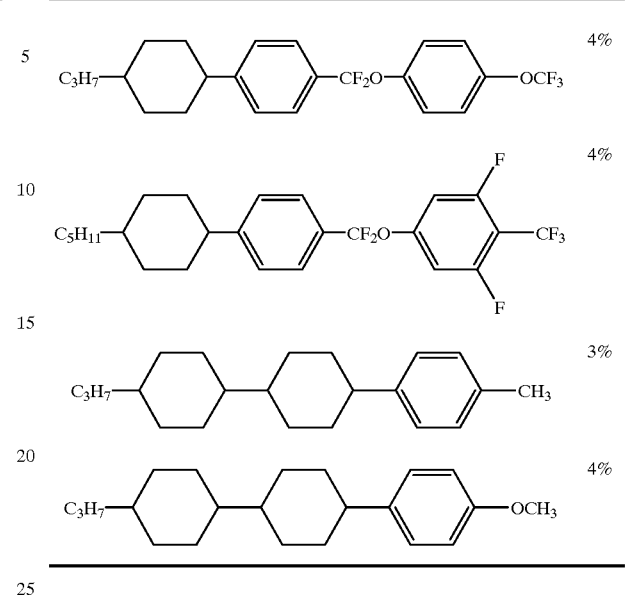

EXAMPLE 10

Using the same polyamic acid as in Example 2, liquid crystal cells were prepared in the same manner as in Example 2 except that the liquid crystal compositions (LF)–(LK) were used as those for STN, the alignment thereof was proved to be satisfactory. Formulations of the liquid crystal compositions (LF)–(LK) as used herein will be shown below.

Liquid Crystal Composition (LF)

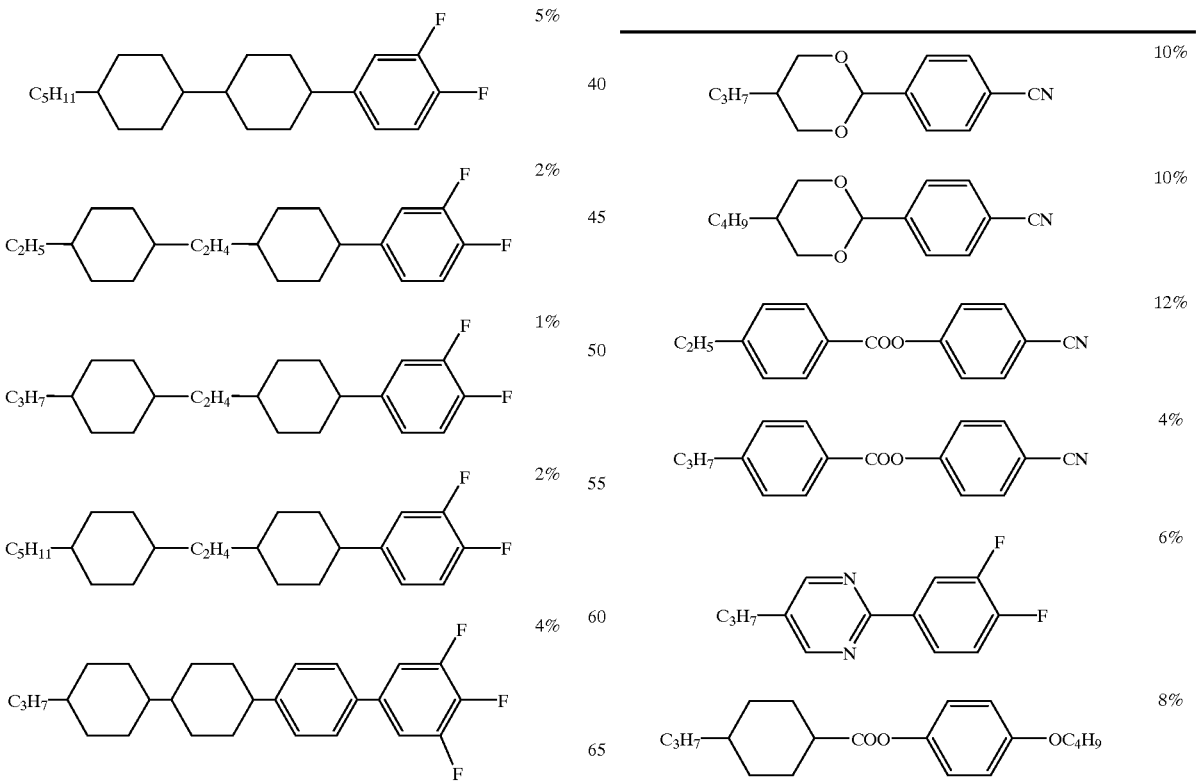

[Structural formula] C₄H₉–(cyclohexyl)–COO–(phenyl)–OC₂H₅  6%

[Structural formula] C₅H₁₁–(cyclohexyl)–COO–(phenyl)–OCH₃  6%

[Structural formula] C₃H₇–(cyclohexyl)–COO–(phenyl)–OC₂H₅  5%

[Structural formula] C₅H₁₁–(cyclohexyl)–COO–(phenyl)–OC₂H₅  4%

[Structural formula] C₅H₁₁–(cyclohexyl)–COO–(phenyl)–C₅H₁₁  5%

[Structural formula] C₄H₉–(cyclohexyl)–COO–(phenyl)–C₅H₁₁  5%

[Structural formula] CH₃O–(phenyl)–COO–(phenyl)–C₂H₅  4%

[Structural formula] C₃H₇–(cyclohexyl)–(cyclohexyl)–(phenyl)–CH₃  6%

[Structural formula] C₃H₇–(cyclohexyl)–(cyclohexyl)–COO–(phenyl)–(phenyl)–CN  3%

[Structural formula] C₃H₇–(cyclohexyl)–(phenyl)–COO–(phenyl)–(phenyl)–CN  3%

[Structural formula] C₅H₁₁–(cyclohexyl)–(phenyl)–COO–(phenyl)–(phenyl)–CN  3%

Liquid Crystal Composition (LG)

[Structural formula] C₂H₅OCH₂–(phenyl)–COO–(phenyl with F)–CN  5%

[Structural formula] C₃H₇OCH₂–(phenyl)–COO–(phenyl with F)–CN  12%

[Structural formula] C₅H₁₁OCH₂–(phenyl)–COO–(phenyl with F)–CN  4%

[Structural formula] CH₃CH=CHC₂H₄–(phenyl)–COO–(phenyl with 2F)–CN  16%

[Structural formula] C₃H₇–(cyclohexyl)–(phenyl)–OC₂H₅  10%

[Structural formula] C₃H₇–(cyclohexyl)–(cyclohexyl)–C₄H₉  3%

[Structural formula] C₃H₇–(cyclohexyl)–(cyclohexyl)–(phenyl)–F  3%

[Structural formula] C₃H₇–(cyclohexyl)–(cyclohexyl)–(phenyl)–CH₃  8%

[Structural formula] C₃H₇–(cyclohexyl)–(cyclohexyl)–(phenyl)–OCH₃  4%

[Structural formula] C₃H₇–(cyclohexyl)–(phenyl)–COO–(phenyl)–F  4%

[Structural formula] C₃H₇–(cyclohexyl)–(cyclohexyl)–COO–(phenyl)–F  7%

[Structural formula] C₅H₁₁–(cyclohexyl)–(cyclohexyl)–COO–(phenyl)–F  7%

[Structural formula] C₃H₇–(cyclohexyl)–C₂H₄–(phenyl)–C≡C–(phenyl)–C₂H₅  4%

[Structural formula] C₃H₇–(cyclohexyl)–C₂H₄–(phenyl)–C≡C–(phenyl)–C₃H₇  4%

-continued

C₃H₇–[Cy]–C₂H₄–[Ph]–C≡C–[Ph]–C₄H₉    4%

C₃H₇–[Cy]–[Ph(3-F)]–C≡C–[Ph]–C₂H₅    5%

Liquid Crystal Composition (LH)

CH₂=CHC₂H₄–[Cy]–[Ph]–CN    12%

CH₃CH=CHC₂H₄–[Cy]–[Ph]–CN    12%

C₃H₇–[Cy]–[Ph]–CN    24%

C₃H₇–[Cy]–[Ph(3-F)]–CN    5%

C₂H₅–[Ph]–C≡C–[Ph]–CH₃    2%

C₃H₇–[Cy]–[Cy]–C₄H₉    8%

C₃H₇–[Cy]–[Cy]–CH=CF₂    6%

C₃H₇–[Cy]–[Cy]–[Ph]–CN    9%

C₃H₇–[Cy]–[Ph(3-F)]–C≡C–[Ph]–C₂H₅    8%

C₃H₇–[Cy]–C₂H₄–[Ph]–C≡C–[Ph]–C₂H₅    5%

-continued

C₃H₇–[Cy]–C₂H₄–[Ph]–C≡C–[Ph]–C₃H₇    5%

C₃H₇–[Cy]–C₂H₄–[Ph]–C≡C–[Ph]–C₄H₉    4%

Liquid Crystal Composition (LI)

C₅H₁₁–[Ph]–COO–[Ph(3-F)]–CN    5%

CH₂=CH–[Cy]–[Ph]–CN    11%

C₅H₁₁–[Pyrimidine]–[Ph]–CN    6%

C₄H₉–[Ph]–[Ph]–C₃H₇    11%

C₃H₇–[Cy]–[Cy]–C₂H₄CH=CH₂    10%

C₅H₁₁–[Cy]–[Cy]–CH=CH₂    11%

CH₂=CH–[Cy]–[Cy]–[Ph]–CH₃    7%

CH₂=CH–C₂H₄–[Cy]–[Cy]–[Ph]–CH₃    15%

C₃H₇–[Cy]–[Cy]–[Ph]–CH₃    9%

CH₃CH=CHC₂H₄–[Cy]–[Cy]–[Ph]–C₂H₅    10%

C₃H₇–[Cy]–[Cy]–COO–[Cy]–C₃H₇    5%

Liquid Crystal Composition (LJ)
| Structure | % |
|---|---|
| 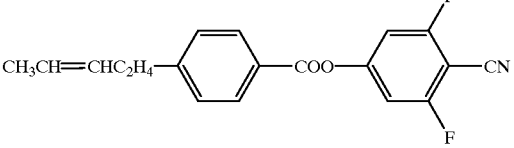 | 6% |
| 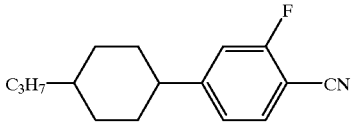 | 18% |
| 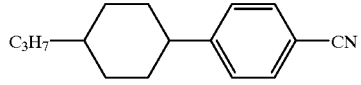 | 10% |
|  | 30% |
| 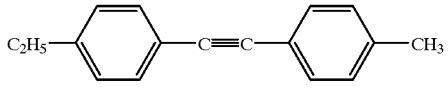 | 8% |
| 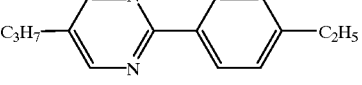 | 11% |
| 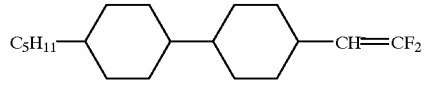 | 5% |
| 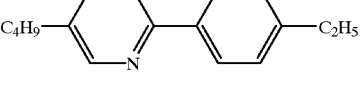 | 4% |
| 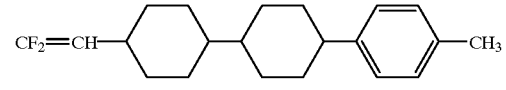 | 4% |
| 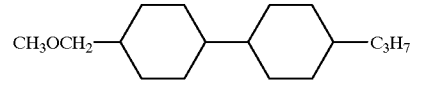 | 4% |
Liquid Crystal Composition (LK)
| Structure | % |
|---|---|
| 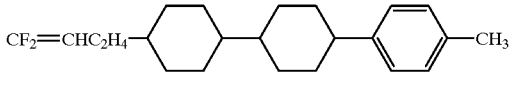 | 18% |
| 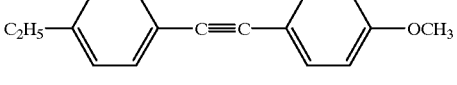 | 3% |
| 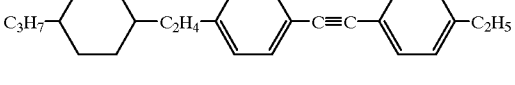 | 10% |
-continued
| Structure | % |
|---|---|
| 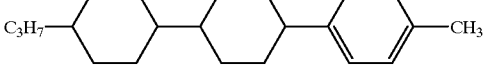 | 10% |
| 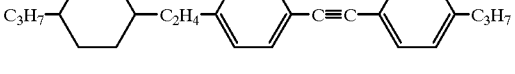 | 2% |
| 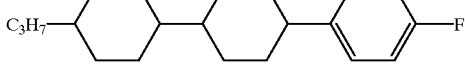 | 2% |
| 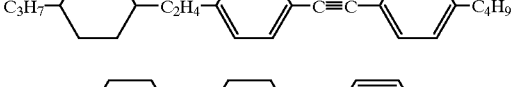 | 2% |
| 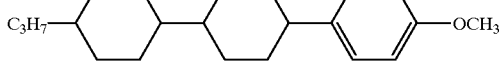 | 7% |
| 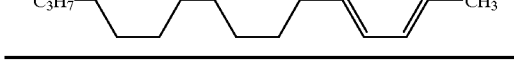 | 7% |
| 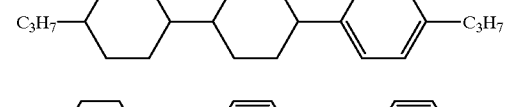 | 7% |
| 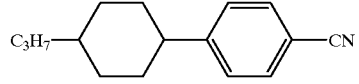 | 4% |
| 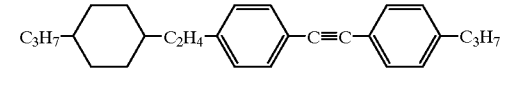 | 4% |
| 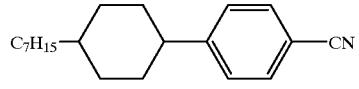 | 8% |
| 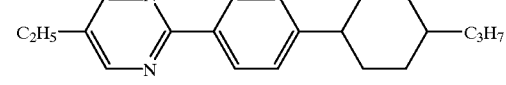 | 3% |
| 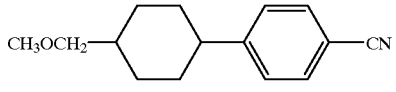 | 3% |
|  | 4% |
|  | 3% |

-continued

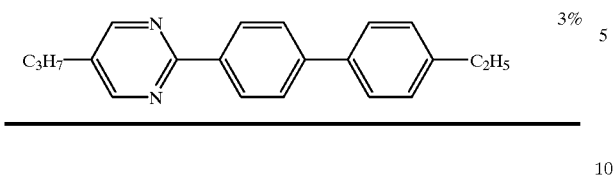

3%

COMPARATIVE EXAMPLE 1

The same procedures as in Example 2 were followed except that the polyimide having the following structural unit was used, and any alignment of the liquid crystal was not observed.

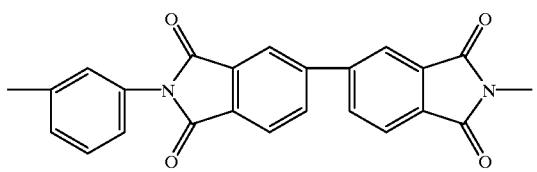

INDUSTRIAL APPLICABILITY

The polyimide derived from the polyamic acid according to this invention which has an α,β-substituted maleimide residue in the side chain thereof has a high sensitivity to polarized ultraviolet light and may rapidly photoreact when said ultraviolet light is irradiated. The film after the photoreaction is excellent in heat stability and shape retaining ability and it is especially useful as an aligning film having a good alignment of liquid crystal.

What is claimed is:
1. A diamino compound represented by the formula [1]:

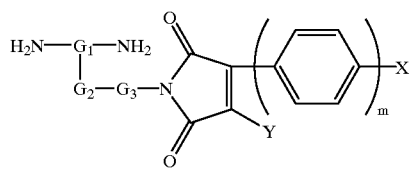

[1]

in which $G_1$ is a trivalent organic group of 2–20 carbon atoms, $G_2$ is independently a single bond, —COO—, —OCO—, —NHCO—, —CONH—, —O—, —S—, or —CO—, $G_3$ is a single bond or an alkylene group of 1–20 carbon atoms, X and Y are each independently a hydrogen atom, a fluorine atom, a chlorine atom, a cyano group, a nitro group, or an alkyl group, a haloalkyl group, an alkoxy group or a haloalkoxy group, each alkyl or alkoxy group having 1–12 carbon atoms, or a cycloalkyl group of 3–8 carbon atoms or a trans-4-alkylcyclohexyl group of 9–14 carbon atoms, and m is an integer of 0–3.

2. A polyamic acid which comprises a structural unit represented by the formula [2]:

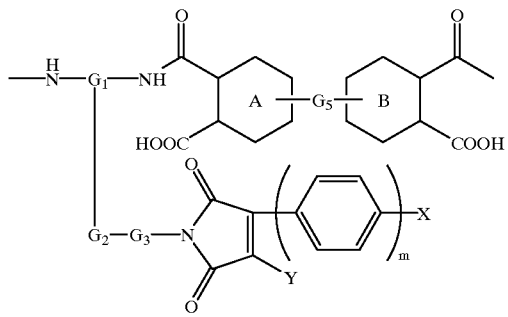

[2]

in which $G_1$, $G_2$, $G_3$, X and Y are as defined in claim 1, $G_5$ is independently a single bond, or a bond of —CH$_2$—, —O—, —CO—, —SO$_2$—, —C(CH$_3$)$_2$— or —C(CF$_3$)$_2$—, and rings A and B are each independently a benzene ring or a cyclohexane ring; and has a logarithmic viscosity number of 0.1–5.0 dl/g as measured in N-methyl-2-pyrrolidone at the concentration of 0.5 g/dl at the temperature of 30±0.01° C.

3. A polyimide obtained by imidation of the polyamic acid as claimed in claim 2 and subsequent irradiation of a polarized ultraviolet light.

4. An aligning film for a liquid crystal display device using a thin film comprising the polyimide as claimed in claim 3.

5. A liquid crystal display device which comprises an aligning film for a liquid crystal display device as claimed in any claim 3.

6. A liquid crystal display device as claimed in claim 5 wherein a liquid crystal composition comprises at least one compound selected from the group consisting of the compounds of the formulae [5], [6] and [7]:

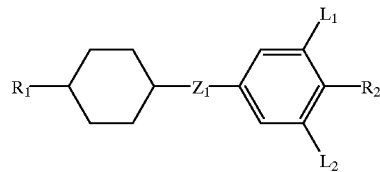

[5]

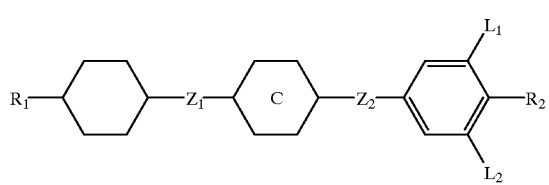

[6]

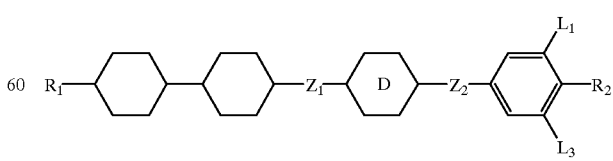

[7]

in which $R_1$ is an alkyl group of 1–10 carbon atoms wherein any non-adjacent methylene groups may be substituted with —O— or —CH=CH— and any hydrogen atoms may be substituted with fluorine atoms; $R_2$ is a fluorine atom, a chlorine atom, —$OCF_3$, —$OCF_2H$, —$CF_3$, —$CF_2H$, —$CFH_2$, —$OCF_2CF_2H$ or —$OCF_2CFHCF_3$; $L_1$ and $L_2$ are each independently a hydrogen atom or a fluorine atom; $Z_1$ and $Z_2$ are each independently 1,2-ethylene, 1,4-butylene, —COO—, —$CF_2O$—, —$OCF_2$—, —CH=CH— or a single bond; ring C is trans-1,4-cyclohexylene, 1,3-dioxane-2,5-diyl or 1,4-phenylene wherein a hydrogen atom may be substituted with a fluorine atom; and ring D is trans-1,4-cyclohexylene or 1,4-phenylene wherein a hydrogen atom may be substituted with a fluorine atom.

7. A liquid crystal display device as claimed in claims 6 wherein a liquid crystal composition further comprises one or more of optically active compounds.

8. A liquid crystal display device as claimed in claim 5 wherein a liquid crystal composition comprises at least one compound selected from the group consisting of the compounds of the formulae [8] and [9]:

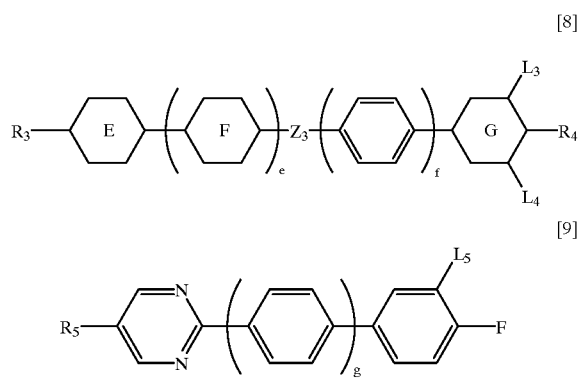

in which $R_3$ and $R_5$ are each independently an alkyl group of 1–10 carbon atoms wherein any non-adjacent methylene groups may be substituted with —O— or —CH=CH— and any hydrogen atoms may be substituted with fluorine atoms; $R_4$ is a group of —CN or —C≡C—CN; ring E is trans-1,4-cyclohexylene, 1,4-phenylene, 1,3-dioxane-2,5-diyl or pyrimidine-2,5-diyl; ring F is trans-1,4-cyclohexylene, 1,4-phenylene wherein a hydrogen atom may be substituted with a fluorine atom, or pyrimidine-2,5-diyl; ring G is trans-1,4-cyclohexylene or 1,4-phenylene; $Z_3$ is 1,2-ethylene, —COO— or a single bond; $L_3$, $L_4$ and $L_5$ are each independently a hydrogen atom or a fluorine atom; and e, f and g are each independently 0 or 1.

9. A liquid crystal display device as claimed in claim 5 wherein a liquid crystal composition comprises at least one compound selected from the group consisting of the compounds of the formulae [10], [11] and [12]:

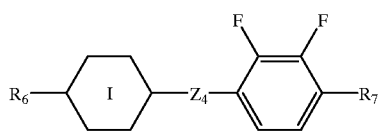

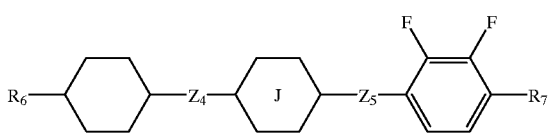

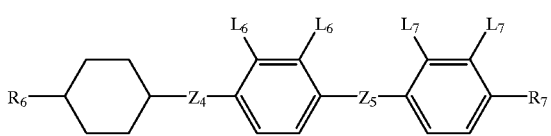

in which $R_6$ and $R_7$ are each independently an alkyl group of 1–10 carbon atoms wherein any non-adjacent methylene groups may be substituted with —O— or —CH=CH— and any hydrogen atoms may be substituted with fluorine atoms; rings I and J are each independently trans-1,4-cyclohexylene or 1,4-phenylene; $L_6$ and $L_7$ are each independently a hydrogen atom or a fluorine atom provided that they do not simultaneously represent hydrogen atoms; and $Z_4$ and $Z_5$ are each independently 1,2-ethylene, —COO— or a single bond.

10. A liquid crystal display device as claimed in claim 5 wherein a liquid crystal composition comprises at least one compound selected from the group consisting of the compounds of the said formulae [5], [6] and [7], and as a second component at least one compound selected from the group consisting of the compounds of the formulae [13], [14] and [15]:

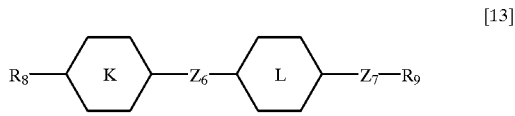

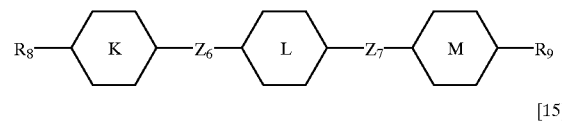

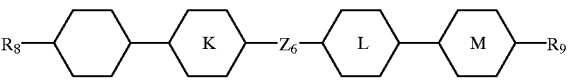

in which $R_8$ and $R_9$ are each independently an alkyl group of 1–10 carbon atoms wherein any non-adjacent methylene groups may be substituted with —O— or —CH=CH— and any hydrogen atoms may be substituted with fluorine atoms; rings K, L and M are each independently trans-1,4-cyclohexylene, pyrimidine-2,5-diyl or 1,4-phenylene wherein a hydrogen atom may be substituted with a fluorine atom; and $Z_6$ and $Z_7$ are each independently 1,2-ethylene, —C≡C—, —COO—, —CH=CH— or a single bond.

11. A liquid crystal display device as claimed in claim 5 wherein a liquid crystal composition comprises at least one compound selected from the group consisting of the compounds of the said formulae [8] and [9], and as a second component at least one compound selected from the group consisting of the compounds of the said formulae [13], [14] and [15].

12. A liquid crystal display device as claimed in claim 5 wherein a liquid crystal composition comprises at least one compound selected from the group consisting of the compounds of the said formulae [10], [11] and [12], and as a second component at least one compound selected from the group consisting of the compounds of the said formulae [13], [14] and [15].

13. A liquid crystal display device as claimed in claim 5 wherein a liquid crystal composition comprises at least one compound selected from the group consisting of the compounds of the said formulae [5], [6] and [7], as a second component at least one compound selected from the group consisting of the compounds of the said formulae [8] and [9] and as a third component at least one compound selected from the group consisting of the compounds of the said formulae [13], [14] and [15].

14. An aligning film for a liquid crystal display device which is obtained by imidation of the polyamic acid as claimed in claim 2, subsequent irradiation of a polarized ultraviolet light and the resulting photoreaction of a portion of the polyimide side chains.

15. A polyamic acid which comprises a structural unit represented by the above formula [2] and a structural unit represented by the formula [3]:

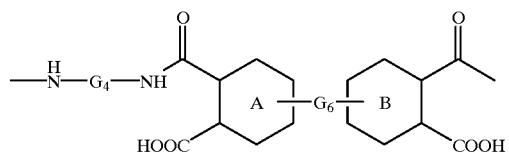

[3]

in which $G_6$ is independently a single bond, or a bond of —$CH_2$—, —O—, —CO—, —$SO_2$—, —$C(CH_3)_2$— or —$C(CF_3)_2$—, rings A and B are each independently a benzene ring or a cyclohexane ring, and $G_4$ is a divalent organic group of 2–36 carbon atoms or a polysiloxane group of the formula [4

]

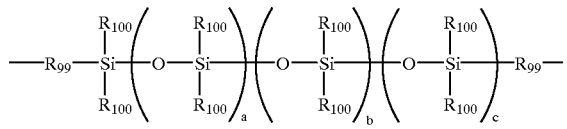

[4]

wherein $R_{99}$ is an alkylene group of 1–6 carbon atoms or a phenylene group, $R_{100}$ independently may be the same or different and is an alkyl group of 1–3 carbon atoms or a phenyl group, and a, b, and c are 0 or a positive number with a relation of $1 \leq a+b+c \leq 100$; and has a logarithmic viscosity number of 0.1–5.0 dl/g as measured in N-methyl-2-pyrrolidone at the concentration of 0.5 g/dl at the temperature of 30±0.01° C.

* * * * *

UNITED STATES PATENT AND TRADEMARK OFFICE
CERTIFICATE OF CORRECTION

PATENT NO. : 6,238,752 B1
DATED : May 29, 2001
INVENTOR(S) : Takashi Kato et al.

It is certified that error appears in the above-identified patent and that said Letters Patent is hereby corrected as shown below:

Column 5,
Third Formula from the top, labeled "[12]", change from

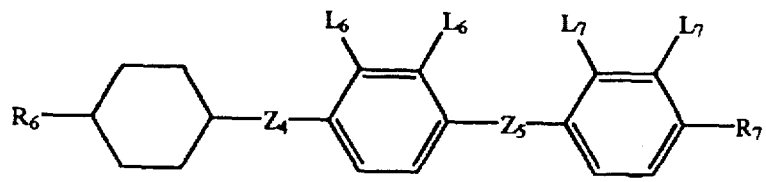

to the following:

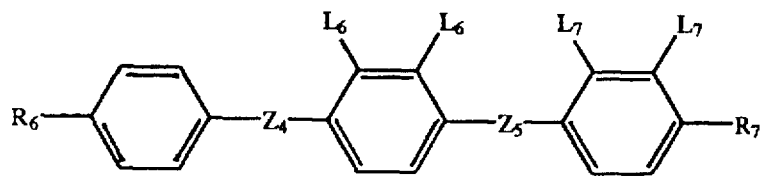

UNITED STATES PATENT AND TRADEMARK OFFICE
CERTIFICATE OF CORRECTION

PATENT NO. : 6,238,752 B1
DATED : May 29, 2001
INVENTOR(S) : Takashi Kato et al.

It is certified that error appears in the above-identified patent and that said Letters Patent is hereby corrected as shown below:

<u>Column 64,</u>
Third Formula, labeled "[12]", change from

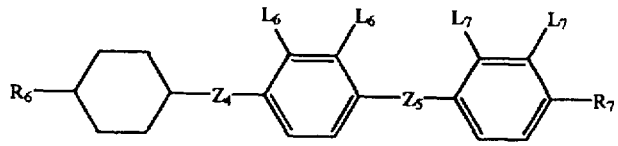

to the following:

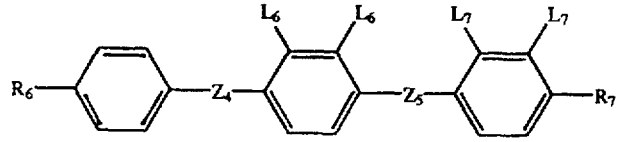

Signed and Sealed this

Twenty-third Day of April, 2002

Attest:

JAMES E. ROGAN
*Attesting Officer*    *Director of the United States Patent and Trademark Office*